United States Patent
Kramer et al.

(10) Patent No.: US 9,816,065 B2
(45) Date of Patent: Nov. 14, 2017

(54) ENVIRONMENTAL PHOTOBIOREACTOR ARRAY (EPBRA) SYSTEMS AND APPARATUS RELATED THERETO

(75) Inventors: David Kramer, Okemos, MI (US);
Robert Zegarac, Okemos, MI (US);
Ben F. Lucker, Okemos, MI (US);
Christopher Hall, East Lansing, MI (US); Casey Abernathy, Olalla, WA (US); Joel Carpenter, Huntsville, AL (US); Jeffrey Cruz, Okemos, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 1056 days.

(21) Appl. No.: 13/988,893

(22) PCT Filed: Nov. 22, 2011

(86) PCT No.: PCT/US2011/061947
§ 371 (c)(1),
(2), (4) Date: May 22, 2013

(87) PCT Pub. No.: WO2012/071467
PCT Pub. Date: May 31, 2012

(65) Prior Publication Data
US 2013/0239461 A1    Sep. 19, 2013

Related U.S. Application Data

(60) Provisional application No. 61/416,250, filed on Nov. 22, 2010.

(51) Int. Cl.
| | |
|---|---|
| *C12N 1/12* | (2006.01) |
| *C12M 1/00* | (2006.01) |
| *C12M 3/00* | (2006.01) |
| *C12M 1/36* | (2006.01) |
| *C12P 7/64* | (2006.01) |

(52) U.S. Cl.
CPC ............. *C12N 1/12* (2013.01); *C12M 21/02* (2013.01); *C12M 23/44* (2013.01); *C12M 23/58* (2013.01); *C12M 41/48* (2013.01); *C12P 7/64* (2013.01)

(58) Field of Classification Search
USPC ................ 435/287.1, 29, 292.1; 44/307
See application file for complete search history.

(56) References Cited

U.S. PATENT DOCUMENTS

| | | |
|---|---|---|
| 7,229,785 B2 | 6/2007 | Seibert et al. |
| 2009/0203067 A1 | 8/2009 | Eckerle et al. |
| 2010/0190235 A1 | 7/2010 | Schuring et al. |
| 2011/0092726 A1* | 4/2011 | Clarke ................ C12M 21/02 554/175 |

FOREIGN PATENT DOCUMENTS

| | | |
|---|---|---|
| WO | 99/46360 A1 | 9/1999 |
| WO | 2010/030658 A2 | 3/2010 |
| WO | 2012/071467 A2 | 5/2012 |
| WO | 2012/071467 A3 | 9/2012 |

OTHER PUBLICATIONS

International Search Report and Written Opinion for PCT Patent Application No. PCT/US2011/061947, mailed on Jul. 18, 2012, 6 pages.
International Preliminary Report on Patentability received for PCT Patent Application No. PCT/US2011/061947, issued on May 22, 2013, 4 pages.

* cited by examiner

*Primary Examiner* — Vishal Vasisth
*Assistant Examiner* — Chantel Graham
(74) *Attorney, Agent, or Firm* — Barbara J. Clark; Clark IP Law, PLC

(57) ABSTRACT

A system is described herein that comprises one or more modular environmental photobioreactor arrays, each array containing two or more photobioreactors, wherein the system is adapted to monitor each of the photobioreactors and/or modulate the conditions with each of the photobioreactors. The photobioreactors are also adapted for measurement of multiple physiological parameters of a biomass contained therein. Various methods for selecting and characterizing biomass are also provided. In one embodiment, the biomass is algae.

38 Claims, 14 Drawing Sheets

US 9,816,065 B2

ENVIRONMENTAL PHOTOBIOREACTOR ARRAY (EPBRA) SYSTEMS AND APPARATUS RELATED THERETO

This application is a U.S. National Stage Filing under 35 U.S.C. 371 from International Application No. PCT/US2011/061947 filed Nov. 22, 2011, and published in English as 2012/071467 on May 31, 2012, which application claims the benefit under 35 U.S.C. 119 (e) of U.S. Provisional Application Ser. No. 61/416,250, filed Nov. 22, 2010, which applications and publications are hereby incorporated herein by reference in their entireties.

STATEMENT OF GOVERNMENT RIGHTS

This invention was made with government support under DE-EE0003046 awarded by the U.S. Department of Energy. The government has certain rights in this invention.

BACKGROUND

A need exists for optimized production of useful products from photosynthetic biomass, such as algae. However, the conditions for such optimized production can vary depending upon the photosynthetic species employed and the environmental conditions available for growth of biomass. Many interrelated factors influence algal photosynthetic biomass bioenergy yield and quality. Moreover, photosynthetic algal biomass can grow very differently in the laboratory, in conventional bioreactors, and in the environment. Current systems used for measuring these variables are bulky, costly and do not yield data on more than one growth variable at a time. Identification of optimal photosynthetic species for growth under selected environmental conditions is currently laborious. Thus, systems are needed for modulating, testing and recording the many variables associated with biomass growth.

SUMMARY

The invention relates to methods, systems and devices that are flexibly adapted to characterize and/or screen different cultured photosynthetic species under a variety of environmental conditions in a cost-effective manner, and thereby identify optimal conditions for growth and production of desirable products from those species. The invention also relates to methods and products generated by the systems and devices.

Accordingly, one aspect of the invention is a system comprising one or more environmental photobioreactor arrays, each array containing two or more modular photobioreactors, wherein the system is adapted:
a) to monitor and modulate conditions within two or more modular of the photobioreactors; and/or
b) to measure one or more physiological parameters of a biomass contained within two or more modular of the photobioreactors.

Another aspect of the invention is a method comprising testing and/or characterizing a biomass using a system comprising one or more environmental photobioreactor arrays, each array containing two or more modular photobioreactors, wherein the system is adapted:
a) to monitor and modulate conditions within two or more modular of the photobioreactors; and/or
b) to measure one or more physiological parameter of a biomass contained within two or more modular of the photobioreactors; and thereby test and/or characterize the biomass.

The method for testing and/or characterizing a biomass using a system can include determining whether a process is rate-limiting in a particular photosynthetic biomass (e.g., a particular algal strain) under a particular set of conditions, in a flexible, cost effective and time-efficient manner.

Another aspect of the invention is a method comprising assessing production of a product from a biomass in a system comprising one or more environmental photobioreactor arrays, each array containing two or more modular photobioreactors, wherein the system is adapted:
a) to monitor and modulate conditions within two or more modular photobioreactors to optimize production of the product; and
b) to measure production of the product under conditions within two or more modular photobioreactors to thereby assess production of the product from a biomass.

For example, the product can be an edible material, pharmaceutical, nutriceutical, protein, amino acid, fat, vitamin, oil, fiber, mineral, sugar, carbohydrate, alcohol or a combination thereof from the biomass. The methods described herein can also include extracting such a product from the biomass.

Another aspect of the invention is a method of extracting a biofuel from a biomass comprising: obtaining an aqueous suspension of biomass (e.g., from a system described herein); adding to said aqueous suspension of biomass at least one organic solvent immiscible or substantially immiscible with water to generate an organic-aqueous mixture; subjecting the organic-aqueous mixture to evaporation of water and biofuel extraction, obtaining: (i) an organic phase comprising biofuels and the organic solvent; (ii) a semi-solid phase comprising a residue of the biomass. Evaporation in such a method can operate at a temperature to yield substantially complete removal of the water from the organic-aqueous mixture. In some embodiments, the biomass is an algal biomass. In some embodiments, the biofuel is a lipid or a mixture of lipids. The solvent can be an aliphatic hydrocarbon, for example, an aliphatic hydrocarbon having a boiling point higher than 100° C. For example, the solvent can be hexane, chloroform, n-octane, nonane, decane, or their mixtures; aromatic hydrocarbons such as xylene isomers, toluene, benzene, chlorobenzene, or their mixtures; refinery cuts including: (a) mixtures of the aliphatic hydrocarbons, where the mixtures have a boiling point higher than 100° C., (b) mixtures of such aromatic hydrocarbons, and (c) mixtures of such aliphatic and aromatic hydrocarbons.

Another aspect of the invention is a biofuel comprising a biomass selected using a system comprising one or more environmental photobioreactor arrays, each array containing two or more modular photobioreactors, wherein the system is adapted:
a) to monitor and modulate conditions within two or more modular of the photobioreactors; and/or
b) to measure one or more physiological parameters of a biomass contained within two or more modular of the photobioreactors.

DETAILED DESCRIPTION OF THE EMBODIMENTS

Figure 1:
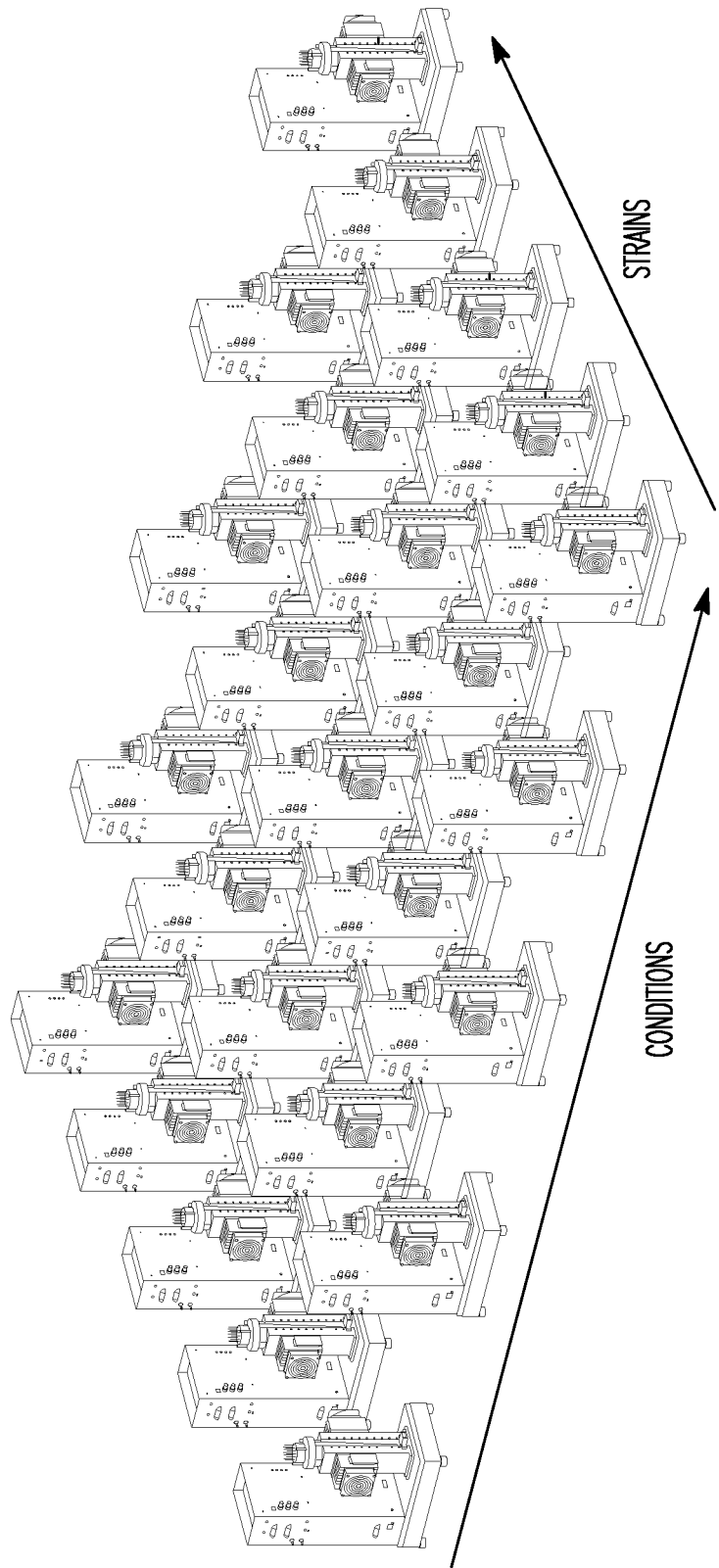
FIG. 1 is a schematic illustration of an environmental photobioreactor array (ePBRA) system in an embodiment of the present invention

The invention relates generally to devices and methods for screening photosynthetic organisms to determine which species (strains) and which conditions provide optimal growth and production of useful products. Such devices and methods involve use of environmental photobioreactor arrays (ePBRA), where multiple parameters can be simultaneously examined to facilitate identification of the species and conditions optimally suited for growth and synthesis of desirable biomass products.

In the following detailed description of the preferred embodiments, reference is made to the accompanying drawings, which form a part hereof, and in which is shown by way of illustration specific preferred embodiments in which the invention may be practiced. These embodiments are described in sufficient detail to enable those skilled in the art to practice the invention, and it is to be understood that other embodiments may be utilized and that chemical, procedural and other changes may be made without departing from the spirit and scope of the present invention. The following detailed description is, therefore, not to be taken in a limiting sense, and the scope of the present invention is defined only by the appended claims, along with the full scope of equivalents to which such claims are entitled.

Definitions

The term "biomass" or "photosynthetic biomass" as used herein, refers to organic matter capable of photosynthesis and harvested or collected from a renewable biological resource as a source of energy. Such biomass includes unicellular and multicellular photosynthetic organisms that can grow in culture. Examples of such biomass include, for example, algae, plant cells, complex algae, such as aquatic macroalgae (e.g. seaweed), aquatic plants, Protista, and prokaryote (e.g. bacteria).

The term "algae" as used herein, refers to any unicellular and/or multicellular photosynthetic organism capable of growing in a liquid culture.

The term "bioreactor" or "environmental photobioreactor (ePBR)" as used herein, refers to a vessel or container used to hold photosynthetic biomass. Such an ePBR is a system that creates an artificial environment to allow photosynthetic biomass to grow. In some embodiments, the ePBR allow photosynthetic biomass to produce useful products. Moreover, the ePBR can be adapted to include environmental and physiological detection and monitoring sensors. For example, the ePBR can be used to screen a variety of environmental conditions so that optimal conditions can be identified for biomass growth and production of useful products.

The term "high-throughput analysis" as used herein, refers to testing in which multiple variables (e.g., factors related to growth and/or productivity) are analyzed simultaneously. "High-throughput analysis" is in contrast to "traditional analysis" in which separate experiments are conducted in which only a single variable is analyzed per experiment. Although generally requiring less automation, traditional analysis requires more time, with the time differential between traditional and high-throughput is related to the number of parameters being analyzed.

The term "biofuel" as used herein, refers to any renewable solid, liquid or gaseous fuel produced biologically, for example, those derived from biomass. Most biofuels are originally derived from biological processes such as the photosynthesis process and can therefore be considered as a solar or chemical energy source.

Overview of Algae Screening

Algae can grow very differently in the laboratory or in conventional bioreactors, as compared to field conditions, such as a production raceway (open pond), due to self-shading, gas mixing, temperature variations, the diurnal cycle, the age of the culture, quorum sensing, and the like.

Because the productivity of the algae depends on many factors optimization of growth and/or product synthesis can depend upon continuous monitoring and/or adjustment of many environmental and/or physiological parameters in the algal culture(s). Although some sensors may be present in conventional photobioreactors, the number and type of sensors may vary from lab to lab and from experiment to experiment. Therefore, conventional photobioreactor systems may not optimally identify the appropriate strains and conditions for biomass and algal product manufacture.

Description of the Embodiments

The novel environmental photobioreactor array (ePBRA) system described herein is sufficiently large to substantially mimic (replicate or reproduce) field conditions, but compact enough to be useful for high throughput analysis. In one embodiment, the ePBRA system comprises an array of modules, each containing an individual environmental photobioreactor (ePBR). As a result, the ePBRA system allows high-throughput parallel growth and phenotypic analyses of a variety of strains of algae under controlled, but variable, growth conditions, while also providing the ability to measure a variety of environmental and phenotypic parameters. Because modules can be added or removed at any time with the ePBRA system, the ePBRA system is also highly flexible and adaptable to accommodate any desired number of sensors.

As will be described further herein, the modules are relatively inexpensive and easy to set up. For example, the costs of the novel ePBRA system described herein are less than current commercial versions (which can cost as much as $60,000 or more). In one embodiment, each module can be set up in a matter of minutes, with an entire array of ePBRs ready for use in 20 minutes or less, as compared with conventional PBRs which require 30 minutes or more of set up time per reactor.

In one embodiment, the novel ePBRA system is modular, with simple ePBR units, which are inexpensive, easy to set up and highly adaptable. Thus, for example, the ePBR units can quickly be set up to flexibly be employed so that many measurements can be taken through a multitude of sensors and the environmental conditions within the ePBR can be adjusted to optimally control temperature, pH, gas mixture, nutrient concentration, light conditions, and combinations thereof. In one embodiment, the design allows detection and standardization of operating conditions so that successful combinations of conditions are easily reproducible in any lab. In some embodiments, various conditions such as temperature, pH, gas mixture, nutrient concentration, light intensity, light/dark cycling and combinations thereof are automated.

FIG. 1 shows a simplified schematic of an ePBRA system for high throughput and standardized measurements of algal properties. In this embodiment, a matrix of ePBR units is configured to allow simultaneous growth of algae (or other species) under varying conditions, while allowing detailed measurements of the physiological status and the environmental condition in each ePBR. In the exemplary embodiment shown in FIG. 1, a condition (e.g., reactor column height) is varied along one axis, while the strain type (e.g. different species, mutants, etc.) is varied along the other axis. In other embodiments, two or more arrays of ePBRs can be employed to simultaneously evaluate several variables at once. For example, variables such as strain type, bioreactor volume, bioreactor configuration, temperature, pH, gas mixture, nutrient concentration, light intensity, light/dark cycling and combinations thereof can be simultaneously monitored and/or evaluated.

The ePBRs can be arranged systemically within arrays or in random locations, to eliminate unexpected variations in conditions.

In some embodiments, the system is designed to accommodate a myriad of sensors. For example, the ePBRs can include sensors such as photodetectors, electrodes, pH electrodes, gas detectors, gas or nutrient sampling devices. Cell density can be monitored by in vivo spectroscopy. Selected sensors can be present within one or more of the ePBRs. For example, the ePBRs can include sensor(s) for detection of temperature, light intensity, light penetration, aeration, $CO_2$ concentration or flow, oxygen concentration or flow, nutrients, cell density, photosynthesis, product production and combinations thereof.

In one embodiment, a wide range of environmental and photosynthetic parameters are measured continuously in a selection of ePBRs within the array. These include, but are not limited to, parameters from chlorophyll fluorescence (saturation-pulse derived values for $F_v/F_M$, phi-2, NPQ, $q_E$, $q_I$, photoinhibition and photorepair, etc.), parameters from absorbance changes induced by light or dark transients including PSI, cytochrome, electrochromic shift, xanthophylls cycle, etc., $CO_2$ gas exchange, dissolved $O_2$ levels, pH, temperature, cell density (via light scattering, transmission at user-defined wavelengths), rough pigment content (via absorbance changes at specific wavelengths), and light penetration through the bioreactor column (via intensity measurements at fixed depths).

The array(s) of ePBRs are part of a system that can store, evaluate and respond to the output from the ePBR sensors. Such a system can facilitate 1) growth of large numbers of algal strains in different ePBRs under multiple conditions (varying temperature, aeration, light, $CO_2$, nutrients, etc.); 2) maintenance of cell densities at optimal levels; 3) continuous measurement of photosynthetic performance and cellular physiology; 4) regulation and adjustment of environmental conditions; 5) detection of endpoint variables (e.g., $O_2$ or $CO_2$ concentrations, cell densities and/or product concentrations); 6) continuous sampling of cells for biomass, energy storage and/or constituent analyses; 7) flexible adjustment of culture conditions to simulate environments of interests (e.g., open ponds of various depths and/or closed bioreactors by varying lighting, mixing, aeration etc.); and 8) adaptability to incorporate additional sensors and input new reagents or factors as new technologies evolve.

In one embodiment, the ePBRA is modular with arrays of separate ePBRs arranged in parallel or in two-dimensional or three-dimensional fashion. Such an ePBRA has the ability to be a phenotyping apparatus, allowing evaluation of a multitude of different species and strains of photosynthetic organisms. Such an array or multi-dimensional array of ePBRs can be arranged and controlled in a single system to coordinate evaluation and modulation of multiple parameters in concert.

In some embodiments, the ePBRAs are modular in sensor type, such that a number of different sensors can be added and controlled simultaneously.

The light source and intensity for each ePBR can be independently varied. In one embodiment, continuous light intensity is supplied by computer-controlled high-intensity white (or colored) light-emitting diodes (LEDs), with an intensity range of 0 to 4000 micromole photons $m^{-2}$ $s^{-1}$ photosynthetically-active radiation. In one embodiment, a photobioreactor system is adapted to illuminate a column of water from the top of the column, thus mimicking sunlight on a natural body of water.

In one embodiment, the pulsed light may be used for chlorophyll fluorescence analysis. For example, a pulsed light intensity (e.g., of one (1) second duration) of at least 15,000 micromole photons $m^{-2}$ $s^{-1}$ can be used.

In one embodiment, each ePBR or group of ePBRs has optional components for separate control of temperature, $CO_2$, aeration, turbidity, pH and light intensity, and can further have optional components for separate control of other variables. For example, the system can include a number of portals for introduction of gases (e.g., air, carbon dioxide, nitrogen and/or oxygen), nutrients (e.g., media, sugars, salts, buffers and the like), test agents (growth modulators, metals, chemicals commonly present in an environment of interest, etc.), and the like. The system can also include extraction sites where culture samples can be withdrawn without substantial modulation of the conditions within the ePBR.

For example, cultures in specific ePBRs can be maintained at selected cell density levels by spectrophotometric monitoring of specific turbidity or light absorbance values (at any visible, ultraviolet or near infrared wavelength) of a culture and computer-controlled dilution with fresh media.

Various media can be used within the ePBR vessels. For example, the media can be any media appropriate for growth, maintenance or testing of a biomass that contains a photosynthetic organism or a photosynthetic cell. Such a biomass can include organisms or cells of a *Protista* or prokaryotic species. For example, the media can be appropriate for growth, maintenance or testing of algae, complex algae, aquatic macroalgae, seaweed, plant cells, aquatic plants or a combination thereof.

In one embodiment, cultures within ePBR vessels can be collected or expelled manually, semi-automatically or automatically as a function of time or other selected variable (e.g., culture density or concentration of a selected product or factor within the culture). Culture aliquots can be frozen using fraction collectors for later analyses of biomass or constituents.

In one embodiment, agitation or stirring is achieved by computer-controlled magnetic stirrer, sparger, computer-controlled bubble-induced flow, or both.

In one embodiment, individual control of temperature is achieved optionally with circulating water baths or electronic heating elements or Peltier-effect coolers.

In one embodiment, the system requires a set up time of less than 20 minutes, such as about 10 to about 20 minutes, such as less than 10 minutes, such as about one minute to about 10 minutes or any range there between. In other embodiments, it is possible that the set-up time may be less than one minute.

In one embodiment a microprocessor or microcontroller is connected to each ePBR to control and/or monitor and/or vary any number of parameters the biomass within is exposed to, and to measure any number of parameters of the exposed biomass and provide a suitable digital output.

In one embodiment, the system includes a processor for storage and or modulation of information received from the ePBR sensors. The system can include software executable on a suitable computer or series of computers connected to the sensors and allows continuous control of all parameters and collection of data and integration of photosynthetic parameters over diurnal cycles or continuous growth.

In one embodiment, environmental data can be "played back" on the ePBR thus simulating previously recorded real environmental data in the individual ePBRs.

In one embodiment, the sensor/environmental control suite is expandable within each ePBR. For example, an ePBR can be adapted to include 1 to 30 sensors. In some embodiments, the ePBR is adapted to include up to eight to 16 sensor ports (or more) on each unit, although the invention is not so limited. Additional ports allow for additional sensors or devices, as needed and available.

In one embodiment, measurements of all parameters can be made both at 1.5 cm from the bottom of the culture or 1 cm from the top of the culture. Such a configuration allows for estimates of light penetration and saturation effects across the entire depth of the culture. In a specific embodiment, culture depth is varied from 5 to 45 cm in a 4.3 cm ID (5 cm OD) glass tube; liquid volume/cm ~14.5 ml. See also FIGS. 2 and 3 described further in Example 1.

In one embodiment, the insert is a modular ePBR vessel which is inexpensive to manufacture, relatively simple to sterilize, assemble and use. In one embodiment, various laboratories can have a desired number of PBR vessels pre-assembled and ready for use. See, for example, FIGS. 4-9, described in more detail below, and in the Examples. In one embodiment, the PBR vessel is autoclavable, thus allowing various laboratories to have a desired number of PBR vessels pre-autoclaved and ready for use.

The vessel can be made of any suitable material, including, but not limited to medical grade plastic, such as polycarbonate, Cyclic Olefin Copolymer (COC), and the like. In one embodiment, the vessel is made from glass.

The ePBR vessel can have any suitable design or configuration. In one embodiment, the sides of the vessels are equipped with thicker plastic 'ribs' to allow custom milling, allowing probes, spargers, media inlets, portals, extraction sites, outlets etc., to be inserted through at any point on the sides of the vessel. In one embodiment, the PBR vessel is slightly conical, and slides inside a sleeve to achieve good thermal contact with a temperature control units. In one embodiment, probes and bubblers are inserted from the top and/or via the side by custom drilling into the plastic "rib" which extends through a gap in the sleeve.

The ePBR vessel can hold liquids such as media for growth of a selected biomass. The volume of the ePBR vessel can vary. In general, the vessels of the modular ePBRs are small enough to be easily removed from an ePBR by one person but large enough to accommodate sufficient volume for biomass culture, growth, sampling and testing over at least one day. For example, the volume of the vessel can vary from about 1 milliliter to about 500 milliliters. In some embodiments, the volume of the vessel can vary from about 2 milliliters to about 300 milliliters or from about 3 milliliters to about 200 milliliters or from about 4 milliliters to about 100 milliliters or from about 5 milliliters to about 50 milliliters.

In one embodiment, as shown in FIGS. 2 through 5, a temperature control unit is used to control temperature and hold an ePBR vessel in place. In this embodiment, the cap allows adequate lighting and the insertion of probes or spargers. In one embodiment, the probes or spargers are typically less than one or two centimeters in diameter. The temperature of the sleeve (and thus the vessel) can be controlled via temperature control units such as Peltier heaters/coolers.

The ePBR can also include a lighting source. In one embodiment, LED lighting is used. In one embodiment, the LED lighting may be attached directly to the ePBR, for example, at the top of vessel so that light shines down through the vessel.

In one embodiment, a novel ePBR system is provided comprising two modular units, namely, a sleeve which controls temperature and contains one or more detectors, and an inner vessel for holding a testing sample, e.g., algae. See, for example, FIGS. 6-9.

Figure 8:
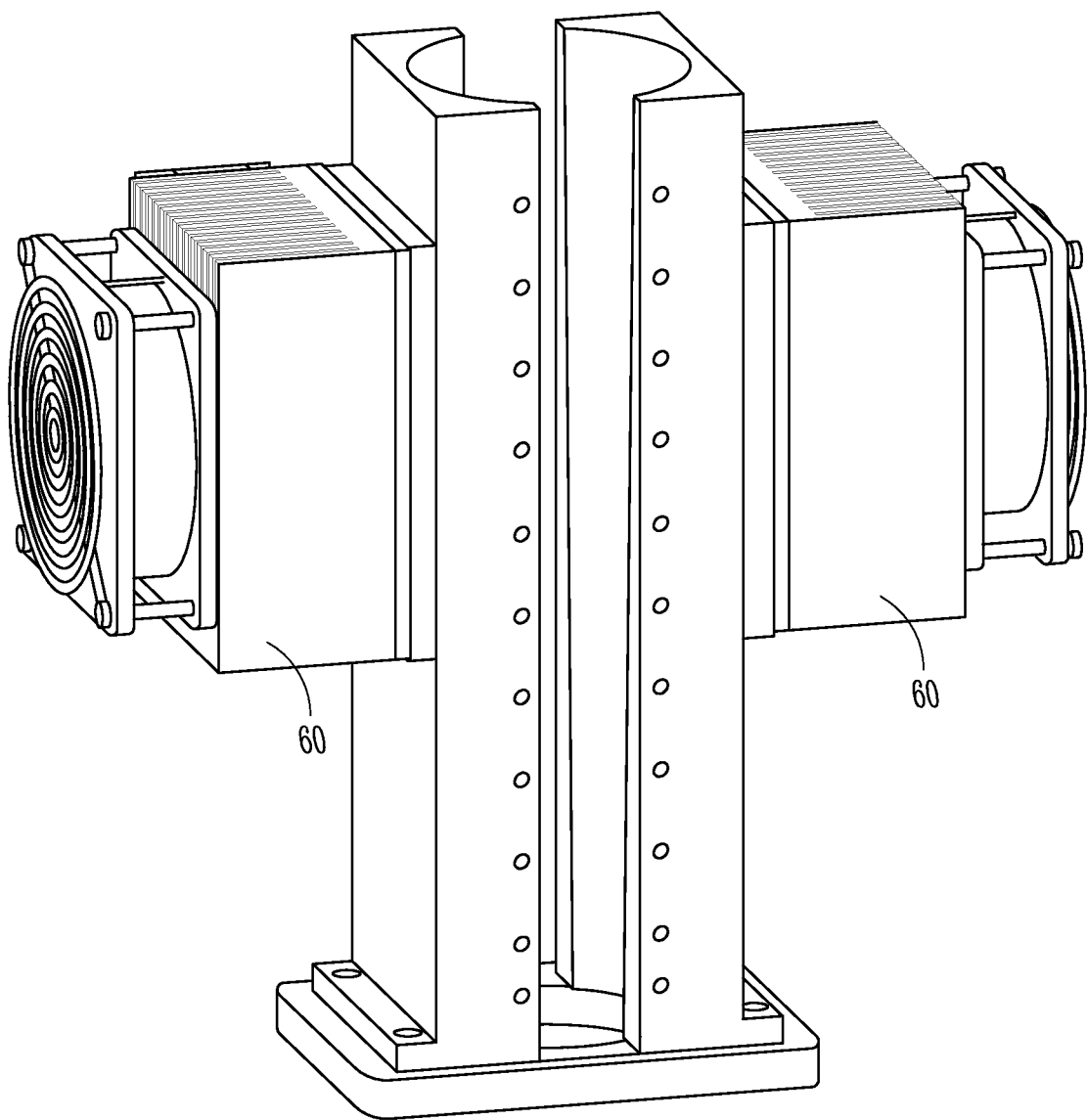
FIG. 8 is a perspective view of a temperature control apparatus of an ePBR system in an embodiment of the present invention.
Figure 9:
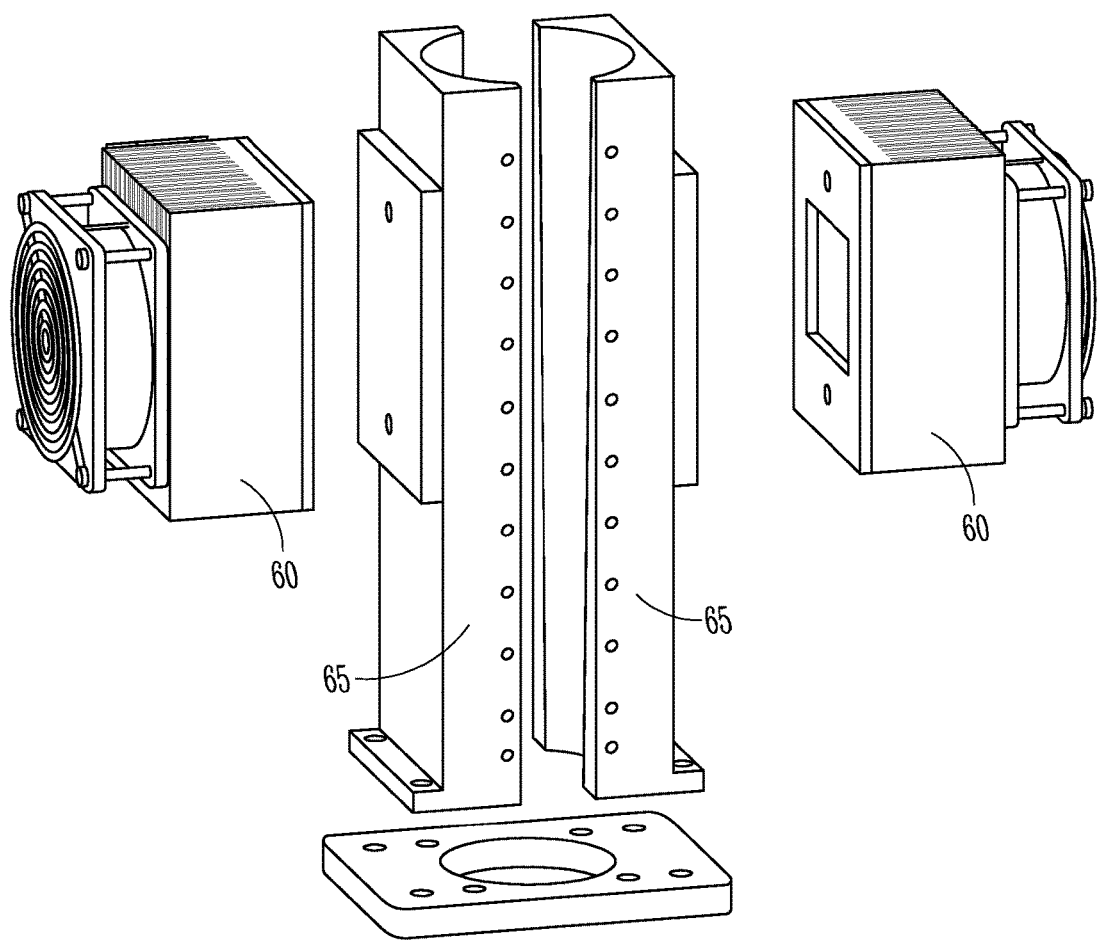
FIG. 9 is a partially dissembled view of the temperature control apparatus FIG. 8 in an embodiment of the present invention.

In one embodiment, such as FIG. 8 the temperature of the vessels is controlled via submersion into a temperature controlled water bath. In one embodiment, the outer sleeve may cover more surface area to allow for better temperature control. In one embodiment, the outer sleeve is hollow, allowing for cooling/heating water flow. The outer sleeve also incorporates a "flat area" for direct contact of electronic heating elements or Peltier-effect coolers, allowing for temperature control of individual PBRs. The outer sleeve can be made of any suitable material. In one embodiment, the outer sleeve is made of cast aluminum, or machined aluminum.

Conditions which can be substantially mimicked or reproduced within each PBR include a raceway system (open pond), as described in the website at algea.ucsd.edu/research/algae-farm.html and algal farming, as described in the website at algaebiodieselfuel.org, although the invention is not so limited.

The ePBRA can be used for a number of applications, including, but not limited to testing the following: various algal strains, mutations in algal strains, growth media, temperature, $CO_2$ levels, $O_2$ levels, gas bubbling rate, intensity or concentration of gas, light intensity, light quality, temporal variations in temperature, injection of chemicals and nutrients, and the like for the purposes of basic research or optimizing photosynthetic production of biofuels, algal aquaculture, pharmaceuticals and the like. The ePBRA can also be used for identifying strains and optimizing conditions for $CO_2$ sequestration, for photosynthetic $CO_2$ scrubbing systems and the like.

The ePBRA can also be used for a number of types of biomass other than algae, including, but not limited to, complex algae, such as aquatic macroalgae (e.g. seaweed), aquatic plants, *Protista,* and prokaryote (e.g. bacteria) for the purposes of basic research or optimizing productivity for optimizing photosynthetic production of biofuels, aquaculture, pharmaceuticals, fermenters and the like.

Figure 14:
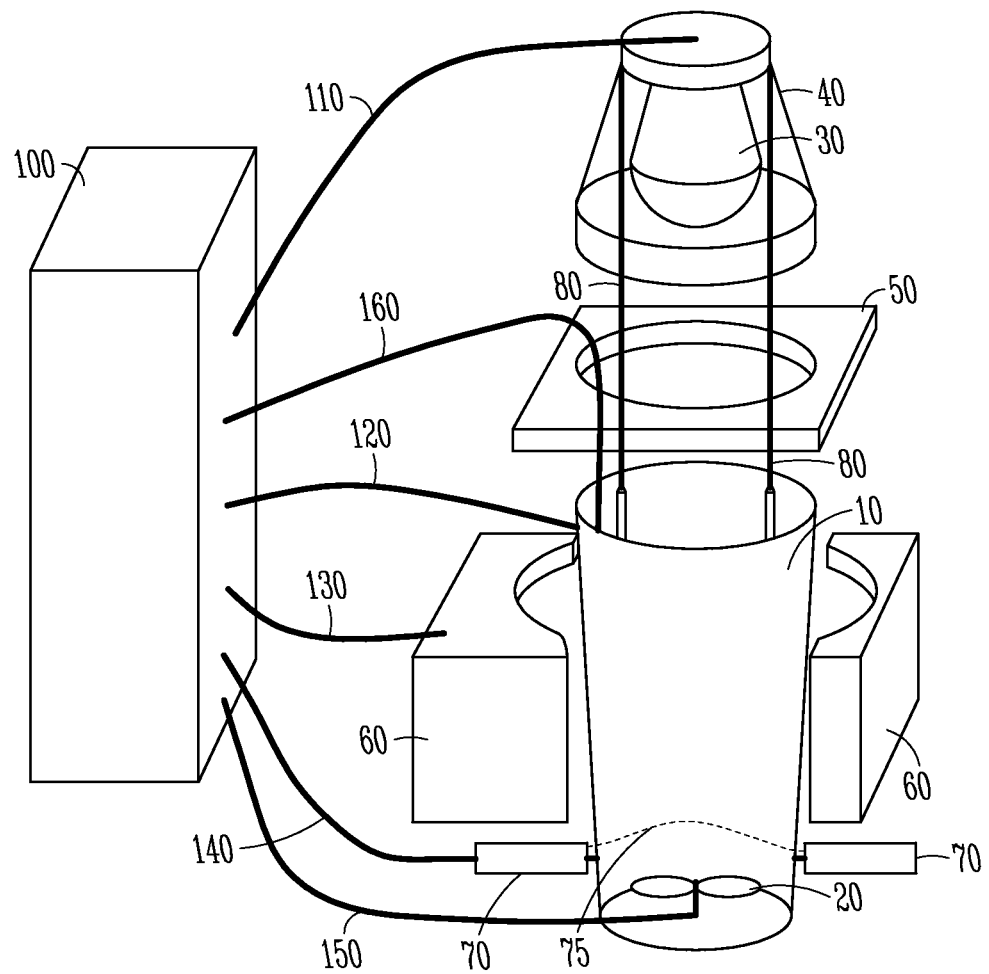
FIG. 14 is a schematic illustration of a system that includes an exemplary modular environmental photobioreactor (ePBR).

By way of illustration, FIG. 14 provides an example of a system where just one modular ePBR is depicted. As described herein, the system includes one or more arrays (ePBRAs), where each ePBRA include at least two modular ePBRs (see, e.g., FIG. 1). However, FIG. 14 permits visualization of one example of the types of components that may be included in an ePBR within such an ePBRA.

In some embodiments, the system includes an array of ePBRs, where each ePBR includes a vessel (10), an agitator (20) and at least one light source (30). The light source (30) can be within a lighting housing (40), which fits into an optical collar (50) that can be affixed to the vessel (10). The vessel can also have an autoclavable lid (55).

The ePBR can also include a number of optional components. For example, the ePBR can include one or more temperature control units (60) for regulating the temperature within the vessel (10). The temperature control units (60) are removable from the vessel (10) but optionally can be affixed to the vessel (10). The temperature control units (60) can each include a jacket (65) that fits around the vessel (10). The ePBR can also include a number of sensors (e.g., 70, 80) for detection of a variety of variables (e.g., environmental conditions within the vessel (10), the physiological status of the biomass within the vessel (10) and/or products synthesized by the biomass within the vessel (10). The system can also include a processor (100) that is operably connected to various components of the system.

As used herein "operably connected" means that the processor can transmit instructions to the components. In some embodiments, the operably connected processor can also receive and process information from components of the system, and transmit instructions back to those components. In some embodiments, the operably connected processor (100) can thereby modulate the environment within the vessel (10), record the status of the environment within the vessel (10) over time and record the growth and status of the biomass, and as well as production of products by the biomass within the vessel (10).

For example, the connector (110) can operably connect the processor (100) to the light source (30) to regulate the intensity and cycling (light/dark) of light within the vessel (10). The connector (110) can also optionally transmit information on the light intensity within the vessel (10), and/or the on-off status of the light to the processor (100), which stores this information.

The connectors, including connector (110) can also be multifaceted. Such a multifaceted connector can such as connector (110) can operably connect one or more sensors (80) to the processor (100). The sensors (80) can detect environmental conditions (e.g., pH, temperature, gas concentration, light intensity, nutrient concentration) and/or biomass status (e.g., secretion of waste and/or products of interest).

In another example, the connector (120) can operably connect the processor (100) to the vessel (10). Such a connector (120) can perform functions similar to the connector (110), for example, detection, monitoring and modulating environmental conditions and/or the status of the biomass in the vessel (10). The connector (120), for example, can allow for transmission of information from a different location within the vessel. Alternatively, the connector (110) and the connector (120) can be programmed to receive different vessel (10) and biomass status information.

In some embodiments, the connector (130) can operably connect the processor (100) to one or more temperature control units (60). For example, the connector (130) can transmit instructions from the processor (100) to one or more temperature control units (60) to warm or cool the vessel (10). In another embodiment, the connector (130) can transmit information from one or more temperature control units (60) to the processor (100), which can process the information and then transmit instructions to one or more temperature control units (60) for regulation of the temperature within the vessel (10).

In some embodiments, the connector (140) can operably connect the processor (100) to a sensor (70) that can have more than one or more components. For example, such a multi-component sensor can have a component that transmits or releases a stimulus and another component that detects a response to the stimulus. The components of the sensor (70) provide coordinated function (transmission/detection) through a connector (75). For example, the sensor (70) can be an optical sensor or an optical probe, where one component transmits light and the other component detects the absorption or fluorescence of the light stimulus. The light absorption or fluorescence information can be transmitted to the processor (100).

The system can also include one or more portal connectors (160) for introducing a liquid and/or a gas. Introduction of a liquid or gas through one or more portal connectors (160) can be initiated by the processor (100) after receipt of information from the sensors. Any liquid and/or gas can be introduced through one or more portal connectors (160). For example, the liquid can include media, test agents, toxins, pharmaceuticals and combinations thereof. Examples of gases that can be introduced through a portal connector (160) include air, oxygen, carbon dioxide, gaseous byproducts of manufacturing and combinations thereof.

In some embodiments, a connector (150) can operably connect an agitator (20) is to the processor (100). Such an operable connection allows the processor to regulate the degree of agitation of the biomass in the vessel (10).

Accordingly, the system can include a number of components including a processor (100), a vessel (10), an agitator (20), a light source (30), one or more temperature control units (60), one or more sensors (70, 80), as well as various connectors between the processor (100) and the various components in the system.

Because the ePBR is a modular unit, the numbers and types of components included in the system can vary. Thus, for example, the temperature control units (60) are removable. In some embodiments, for example, the system can be operated without the temperature control units (60) at ambient temperature, or in a test environment where the ability of the biomass to respond to environmental temperatures or variations thereof is an aspect of a testing procedure.

In other embodiments, the light source (30) can be removed and can be replaced by a larger light source that illuminates a number of ePBRs in an array. In other embodiments, one or more sensors can be used or removed as desired by those of skill in the art.

Another aspect of the invention is a method involving selecting and/or characterizing biomass using a system that includes one or more modular environmental photobioreactor arrays, each array containing two or more photobioreactors, wherein the system is adapted to monitor and modulate conditions within each of the photobioreactors, and wherein the system is adapted to measure multiple parameters of within one or more of the photobioreactors and/or the system is adapted to measure multiple parameters of a biomass contained in the two or more photobioreactors.

In addition to monitoring the environment within an ePBR vessel, the methods and systems described herein can monitor and/or measure the status of the biomass within the ePBR vessels. Parameters relating to the status of a biomass within the ePBR vessels include, the biomass density (e.g., cell density), the biomass growth rate, the photosynthetic activity of the biomass, the production of products by the biomass, the secretion of products by the biomass, the waste produced by the biomass, the absorption of nutrients, toxins, carbon dioxide, pharmaceuticals etc. by the biomass, the processing of nutrients, toxins, carbon dioxide, pharmaceuticals etc. by the biomass, and the like.

Useful Products

The systems and methods described herein can also be adapted to generate useful products from the biomass. Such useful products can include edible materials, pharmaceuticals, nutriceuticals, proteins, amino acids, fats, lipids, oils, vitamins, fiber, minerals, sugars, carbohydrates, alcohols, biofuels or a combination thereof.

One aspect of the invention is therefore a method of extracting a biofuel from a biomass comprising: obtaining an aqueous suspension of biomass; adding to said aqueous suspension of biomass at least one organic solvent immiscible or substantially immiscible with water to generate an organic-aqueous mixture; subjecting the organic-aqueous mixture to evaporation of water and biofuel extraction, obtaining: (i) an organic phase comprising biofuels and the organic solvent; (ii) a semi-solid phase comprising a residue of the biomass. Evaporation in such a method can operate at a temperature to yield substantially complete removal of the water from the organic-aqueous mixture. In some embodiments, the biomass is an algal biomass. In some embodiments, the biofuel is a lipid or a mixture of lipids. The solvent can be an aliphatic hydrocarbon, for example, an aliphatic hydrocarbon having a boiling point higher than 100° C. For example, the solvent can be hexane, chloroform, n-octane, nonane, decane, or their mixtures; aromatic hydrocarbons such as xylene isomers, toluene, benzene, chlorobenzene, or their mixtures; refinery cuts including: (a) mixtures of the aliphatic hydrocarbons, where the mixtures have a boiling point higher than 100° C., (b) mixtures of such aromatic hydrocarbons, and (c) mixtures of such aliphatic and aromatic hydrocarbons.

Another aspect of the invention is a biofuel generated from a system comprising one or more environmental photobioreactor arrays, each array containing two or more modular photobioreactors, wherein the system is adapted:

a) to monitor and modulate conditions within two or more modular of the photobioreactors; and/or b) to measure one or more physiological parameters of a biomass contained within two or more modular of the photobioreactors.

The invention will be further described by reference to the following examples, which are non-limiting and offered to further illustrate various embodiments of the present invention. It should be understood, however, that many variations and modifications may be made while remaining within the scope of the present invention.

EXAMPLE 1

Algal Growth Under Constant vs. Fluctuating Light

Figure 10:
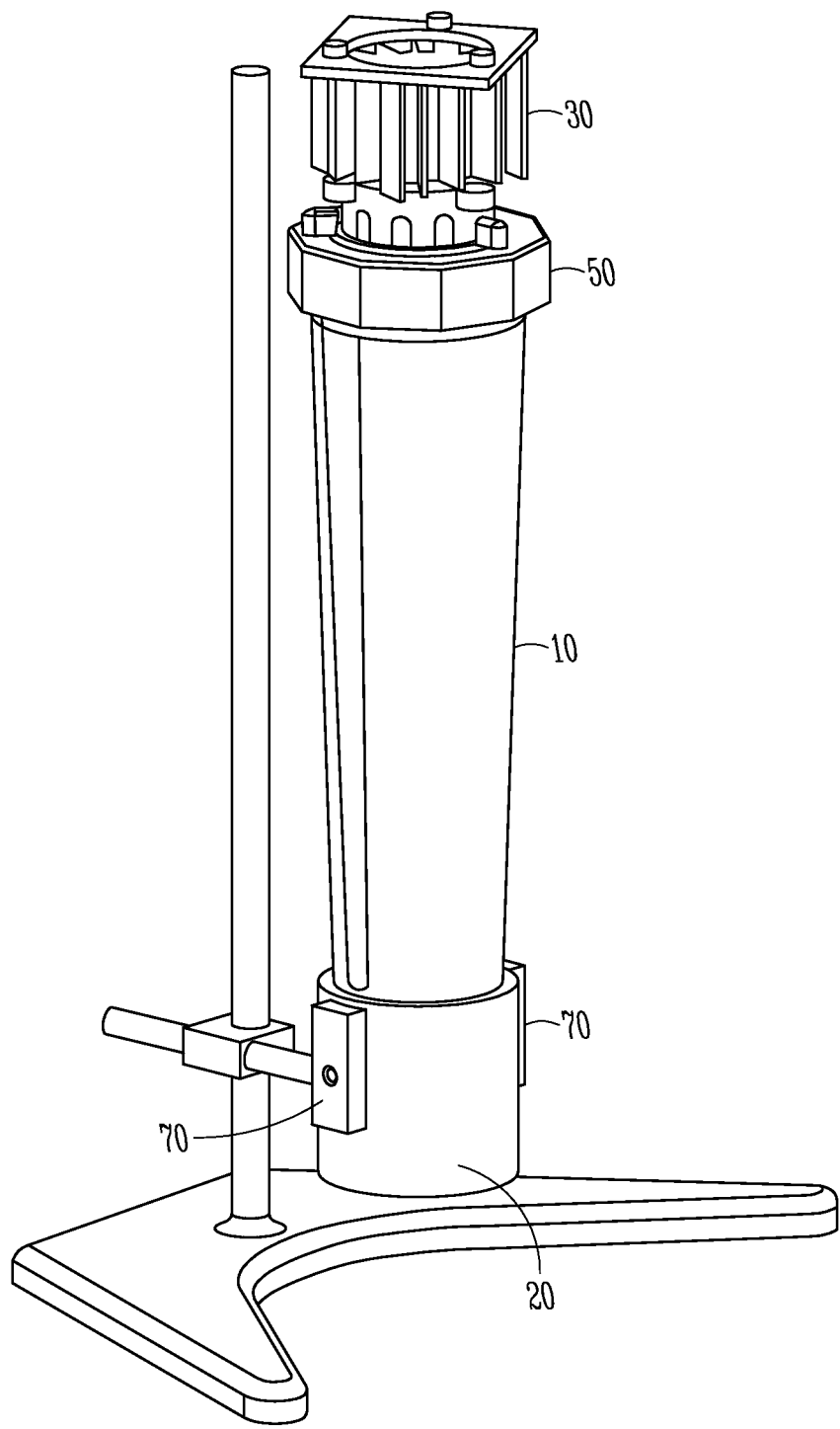
FIG. 10 is a view of ePBR system without a temperature control apparatus in an embodiment of the present invention.
Figure 11:
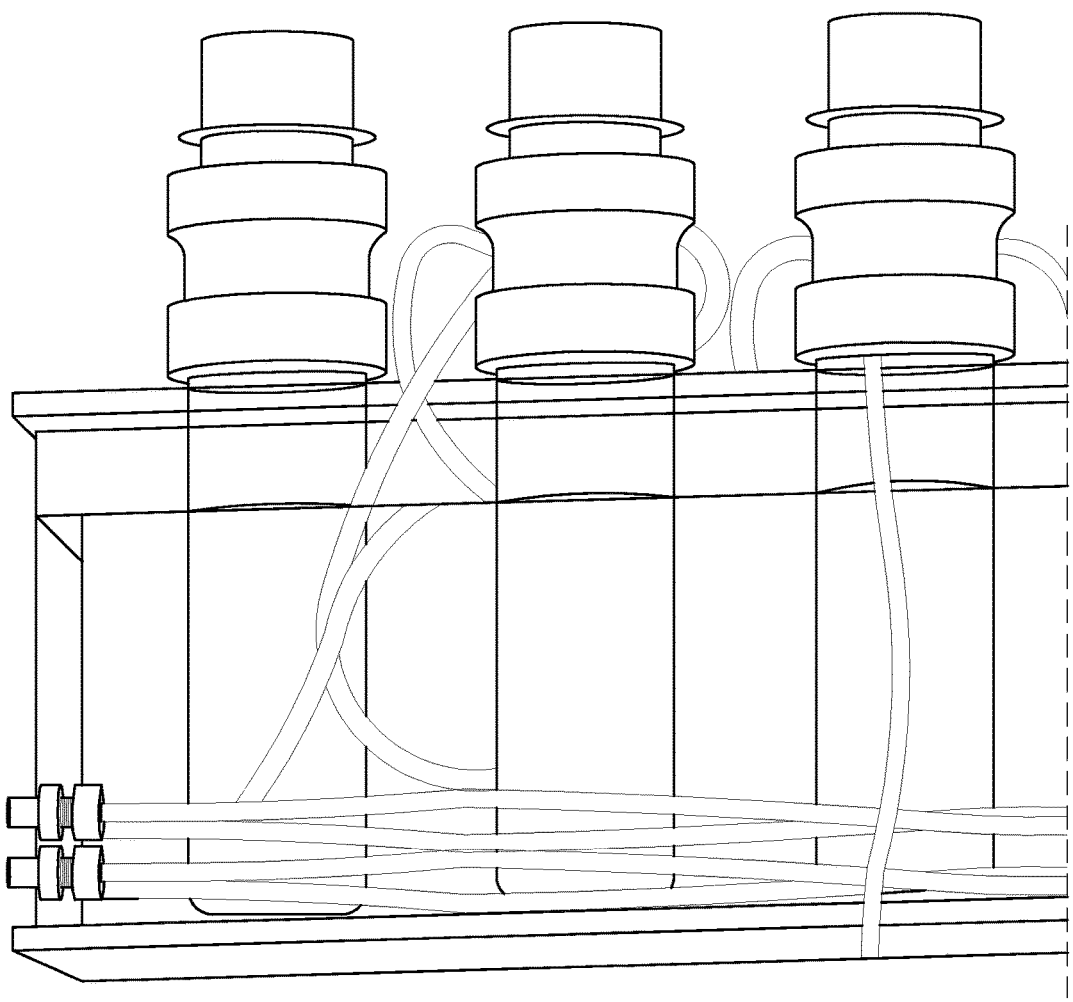
FIG. 11 is an image of an ePBR system with a temperature controlled water bath for temperature control in an embodiment of the present invention.

The tests described in this Example were conducted using a non-temperature controlled system shown in FIG. 10. A study was performed with a matrix of four (4) photobioreactors to determine whether growth rates varied between algae that grew under continuous light and algae that grew under a simulated diurnal cycle.

Experimental Objectives:

1) Observe the difference in growth rates between algae grown under continuous light vs. grown under light that follows a day-night pattern.

2) Testing algal growth reproducibility between reactors.

Materials and Methods:

Four (4) PBR culture vessels were each filled with 520 mL 2NBH medium (Table 1) and sterilized by autoclaving for 20 minutes.

TABLE 1

2NBH Media

| Component | Concentration |
| --- | --- |
| $NaNO$ | 6 mM |
| $CaCl_2 * 2H_2O$ | 0.17 mM |
| $MgSO_4 * 7H_2O$ | 0.3 mM |
| $K_2HPO_4$ | 0.43 mM |
| $KH_2PO_4$ | 1.29 mM |
| NaCl | 0.43 mM |
| Hutners trace elements | 1 × Concentration |

The vessels were inserted into a PBR assembly like the one depicted in FIG. 10.

Each PBR was inoculated with $2.4 \times 10^5$ cells of actively growing *Chlorella sorokiniana* grown in 2NBH medium, to yield an initial starting cell concentration of 240,000 cells per mL.

The conditions within all reactors were controlled via computer software. Reactors were bubbled with air for 1 minute every ten minutes at a rate of 0.50 liters per minute and with a stirring rate of 400 rpm. PBR1 and PBR2 were programmed to simulate the Gaussian light intensity distribution of the sun over a 12 hr diurnal cycle, with a peak light intensity at noon of 2000 µE photosynthetically active radiation. PBR3 and PBR4 were programmed to illuminate continuously but with a light intensity equivalent to the 24 hr integration of light intensity for PBR1 and PBR2. Thus, the total light within the reactors was approximately the same for all of the PBR1-PBR4 reactors (500 µE photosynthetically active radiation). Turbidity measurements were obtained via absorption of pulsed 940 nm light from a standard LED (epoxy lens, 5 mm diameter, 5-8 degree dispersion) through the culture by a silicon phototransistor detector. Circuitry on the printed circuit board (PCB) of each reactor converted the light transmission into a voltage measurement and then sent the measurements to the control computer via TCP internet protocol.

Figure 12:
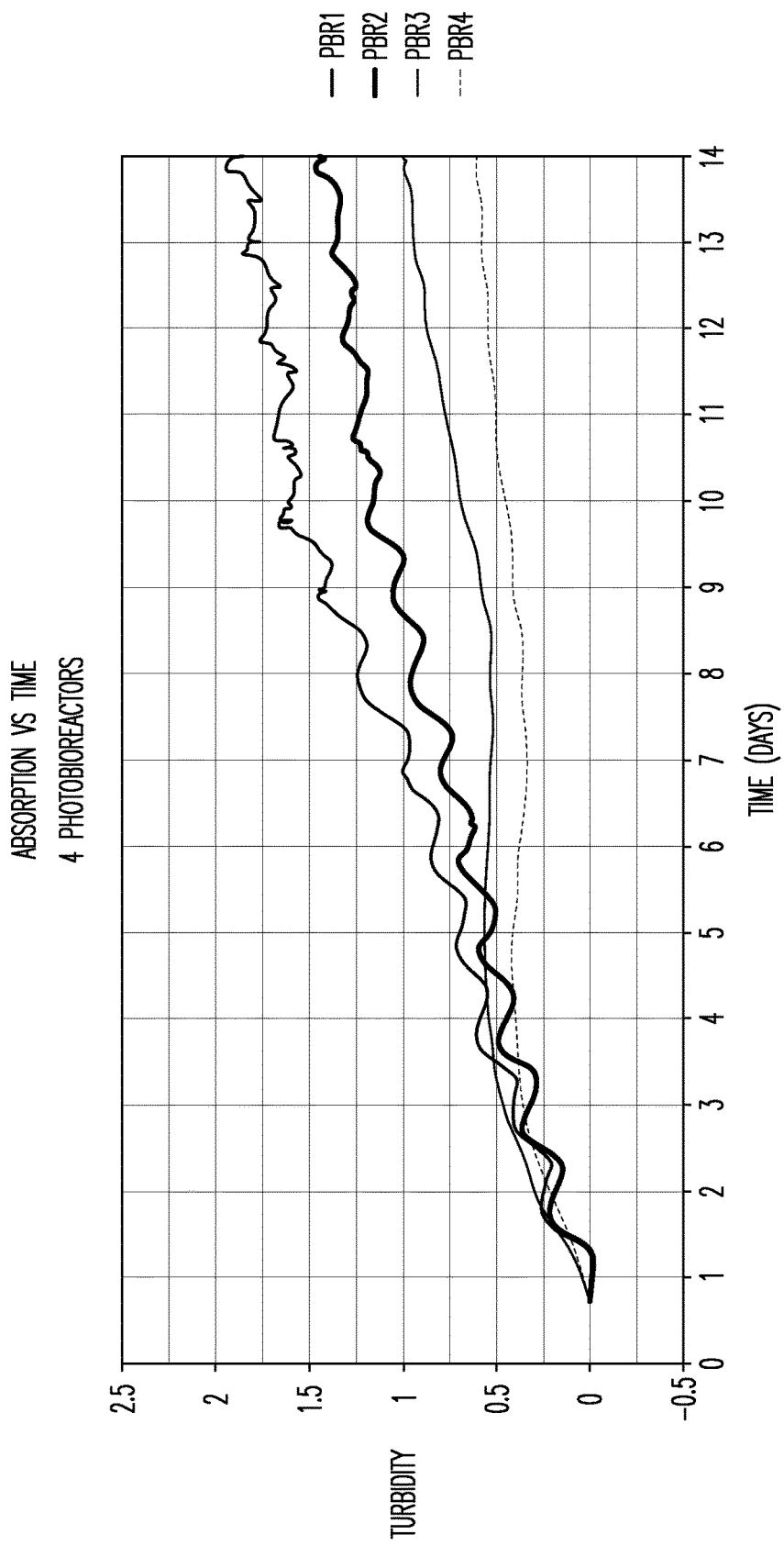
FIG. 12 is a graph showing turbidity measurements of cultures grown over time under sinusoidal diurnal cycles versus constant light intensity in embodiments of the present invention. The results for PBR1 are shown as the solid mid-weight top line; the results for PBR2 are shown as the heavy weight line below the PBR1 line; the results for PBR3 are shown as the light weight line below the PBR2 line; and the results for PBR4 are shown as the dashed line at the bottom.

Results:

As shown in FIG. 12, cultures grown under a simulated natural day-night cycle had more rapid initial growth during the day and more net growth at the end of the experiment than the cultures that received constant light. Unexpectedly, the turbidity decreased during the night in the cultures grown under simulated natural day-night cycles, possibly due to changes in cell size and/or content while the algae consumed the energy that they stored during the day. Both of the continuous light cultures demonstrated a lag phase in their growth behavior after the third day of continuous light and the lag phase persisted for about a week before growth resumed.

These experimental results indicate the following:

1) *Chlorella sorokiniana* grown under simulated day-night cycles will synchronize their growth to grow rapidly during the day and not during the night;

2) On the timescale of 2 weeks, *Chlorella sorokiniana* appears to grow faster with simulated day-night light cycles than under continuous light, even when they receive the same amount of photons; and 3) Turbidity is not a perfect measurement of cell concentration, even within the same culture, because the scattering and absorption coefficients of algal cells are influenced by more factors than just the cell concentration. At least one of these other factors is synchronized in *Chlorella sorokiniana* to the time of day. Therefore, when comparing growth curves, only measurements from the same time of day should be used, or linear averages of the absorption plots.

EXAMPLE 2

Controlling Algal Culture pH with Carbon Dioxide

Figure 2:
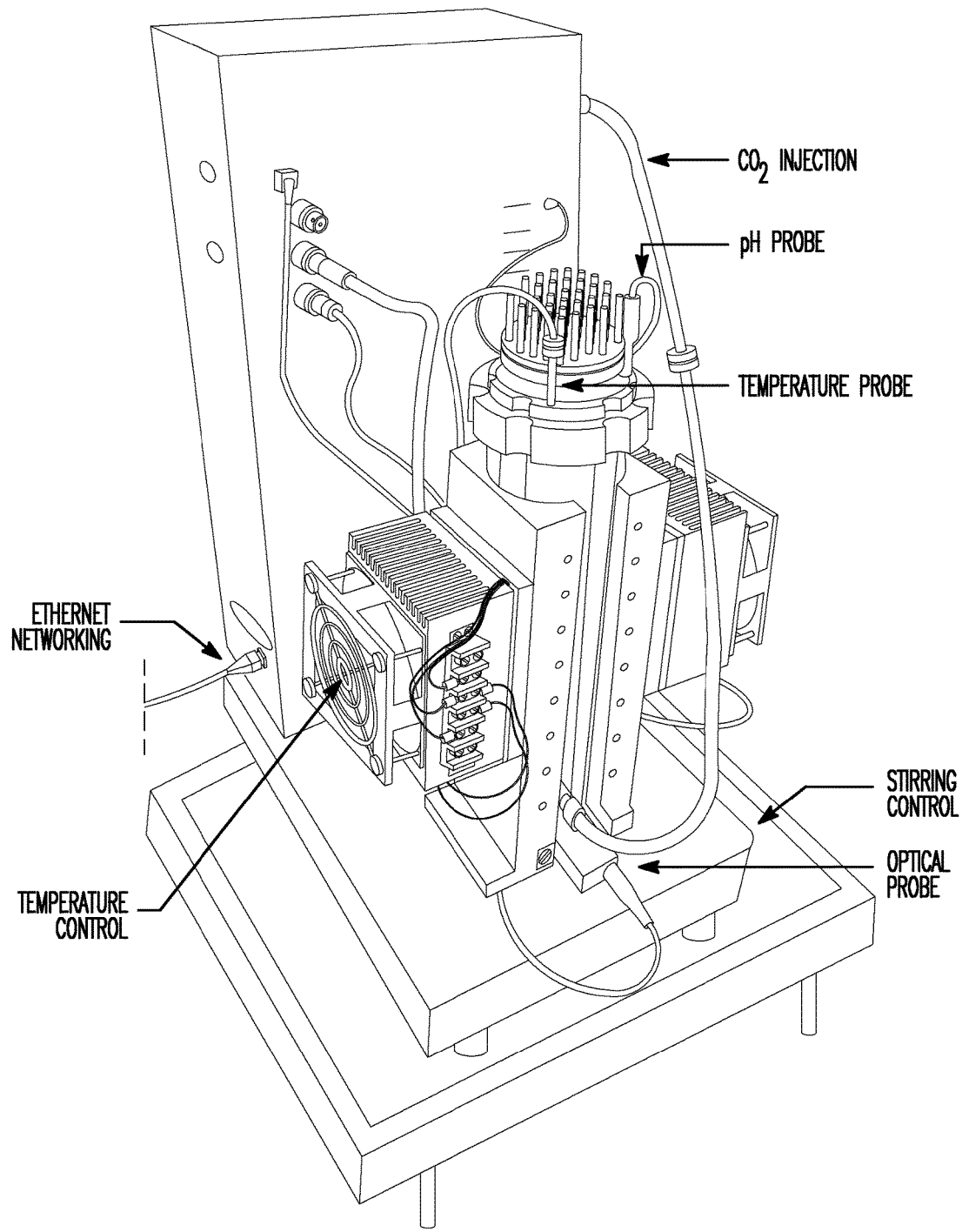
FIG. 2 is a photograph of an environmental photobioreactor (ePBR) system in an embodiment of the present invention.

The tests described herein were conducted using the systems shown in FIG. 2. A study was performed with a single photobioreactor to control supplemental carbon dioxide ($CO_2$) based on feedback from the PBR. This study served as a proof of concept that the computer control software allows for complex control of photobioreactor parameters.

Experimental Objectives:

1) Determine if pH control using $CO_2$ injection is operational.

2) Control the photobioreactor with an event-response program.

Materials and Methods:

One PBR vessel containing 550 mL of sterile 2NBH medium was inserted into a PBR assembly as depicted in FIG. 2 and inoculated with *Chlorella sorokiniana*.

The culture was maintained at constant temperature of 30° C. with illumination in a simulated 12 hr diurnal cycle and a peak noontime intensity of 2000 µE photosynthetically active radiation. The culture was stirred continuously with a magnetic stir bar rotating at 200 RPM. Turbidity, temperature, and pH measurements were taken approximately every minute. The pH was controlled via $CO_2$ injection. When the pH of the culture reached 7.5, a mixture of air with 14% $CO_2$ was injected at 580 sccm until the pH of the culture reached 6.8.

Figure 13:
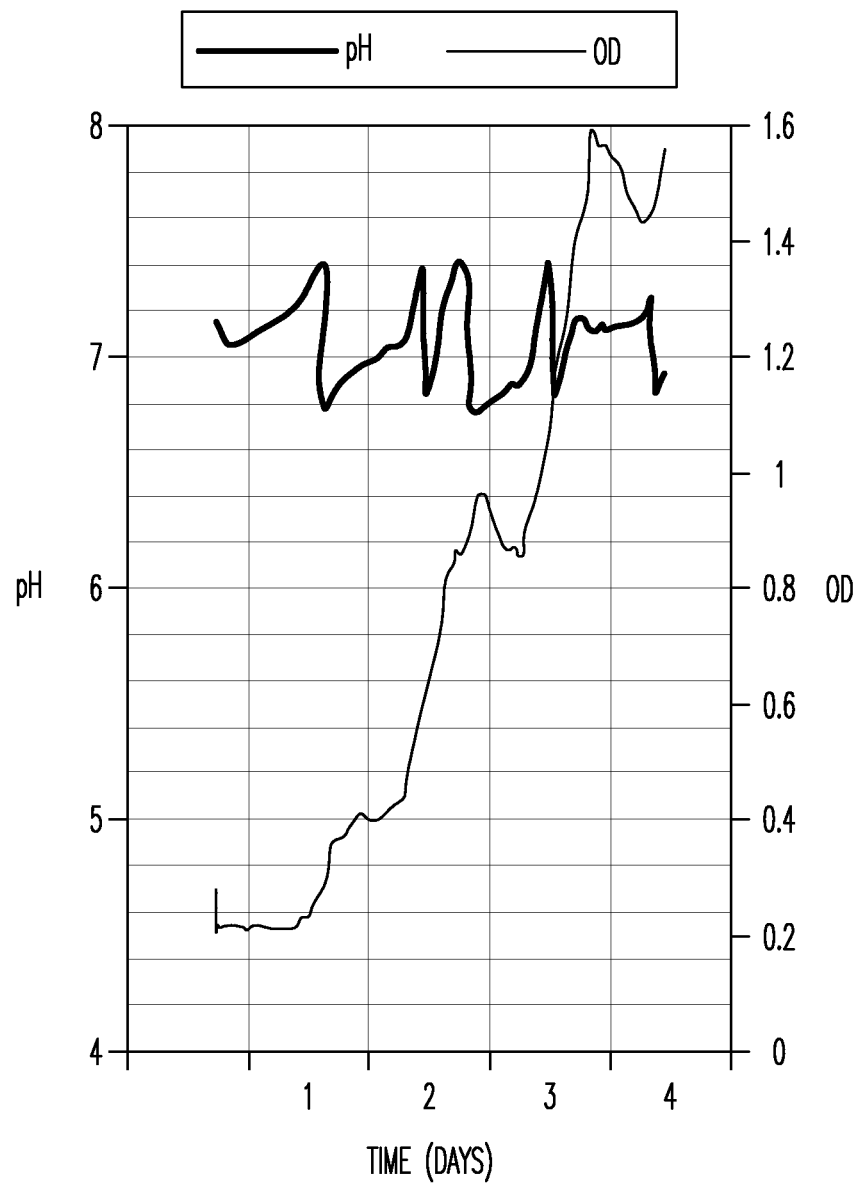
FIG. 13 is a graph showing pH control using $CO_2$ injection and subsequent increase in optical density as a result of growth. The pH readings are shown as the heavy line while the optical density of the biomass is shown as the lighter line.

Results:

FIG. 13 shows that the pH rose faster during the simulated day conditions when the algae were growing faster and photosynthesis was occurring. During the simulated nighttime conditions, the pH initially decreased and then rose very slowly when the algae were not growing significantly and were not undergoing significant photosynthesis. As a result, $CO_2$ injection was triggered only during the day and caused rapid drops in the pH.

These experimental results indicate the following:

1) The PBR was able to make real-time decisions from its sensor data to perform feedback adjustment of culture conditions;

2) pH and photosynthetic growth were correlated for cultured *Chlorella sorokiniana*.

EXAMPLE 3

Algal Growth under Constant versus Fluctuating Temperatures

The tests described herein were conducted using the systems shown in FIG. 2.

Experimental Objectives

1) Demonstrate the ability of the photobioreactor to simulate temperature fluctuations as well as light fluctuations.

2) Determine whether the growth of *Chlorella sorokiniana* is correlated to temperature cycling as well as light cycling.

Materials and Methods

Two (2) PBR vessels were each filled with 540 mL of sterile 2NBH medium (described in Table 1). The vessels were inserted into a PBR (e.g., as depicted in FIG. 2) and programmed to simulate the Gaussian light intensity distribution of the sun over a 12 hr diurnal cycle, with a peak light intensity at noon of 2000 µE photosynthetically active radiation. The pH was maintained between 7.3 and 6.8 by injecting $CO_2$ enriched air (14% $CO_2$ in air) at a rate of 0.58 liters per minute when the pH rose above 7.3 until it dropped back to 6.8. One of the PBRs was programmed to fluctuate its temperature from 22° C. to 38° C., scheduled such that the coldest temperature occurred at 6am and the warmest temperature occurred at 6 pm of each day. The other PBR maintained a constant temperature of 30° C. The culture vessels were inoculated with *Chlorella sorokiniana* to a starting concentration of 300,000 cells per mL.

EXAMPLE 4 (PROPHETIC)

High-Intensity Light Responses

Figure 3:
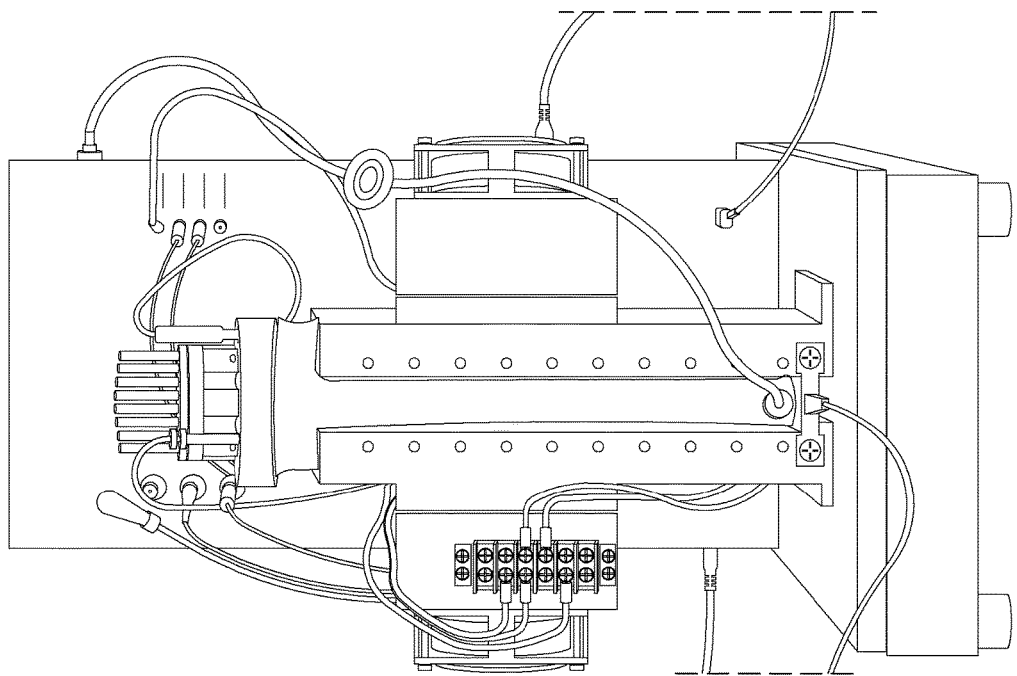
FIG. 3 is a photograph of two ePBR systems in an embodiment of the present invention.
Figure 3:
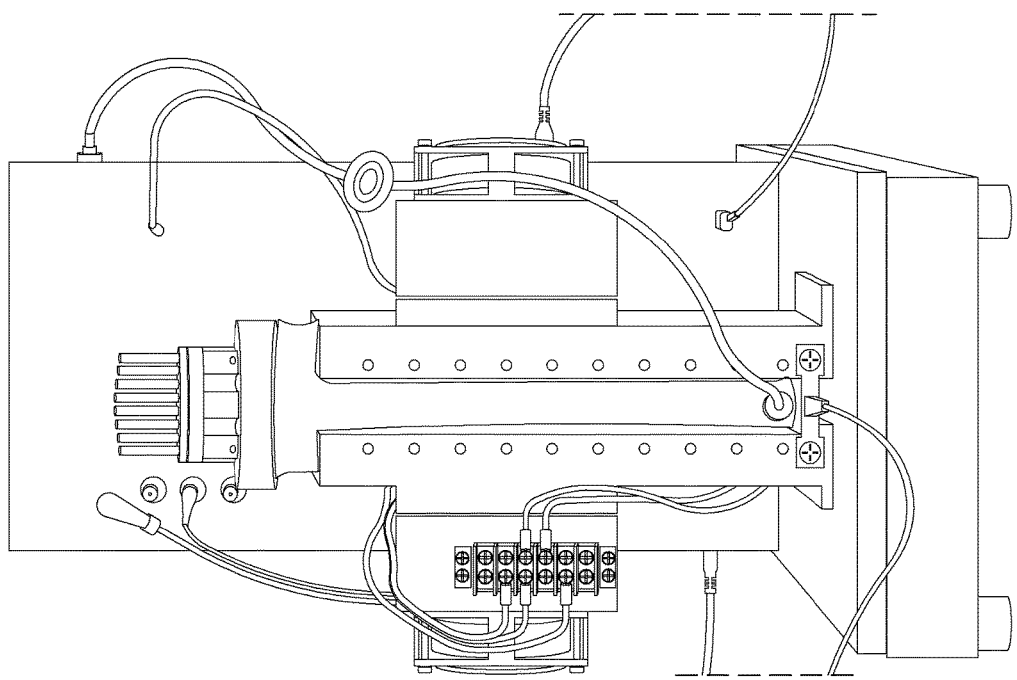
Figure 4:
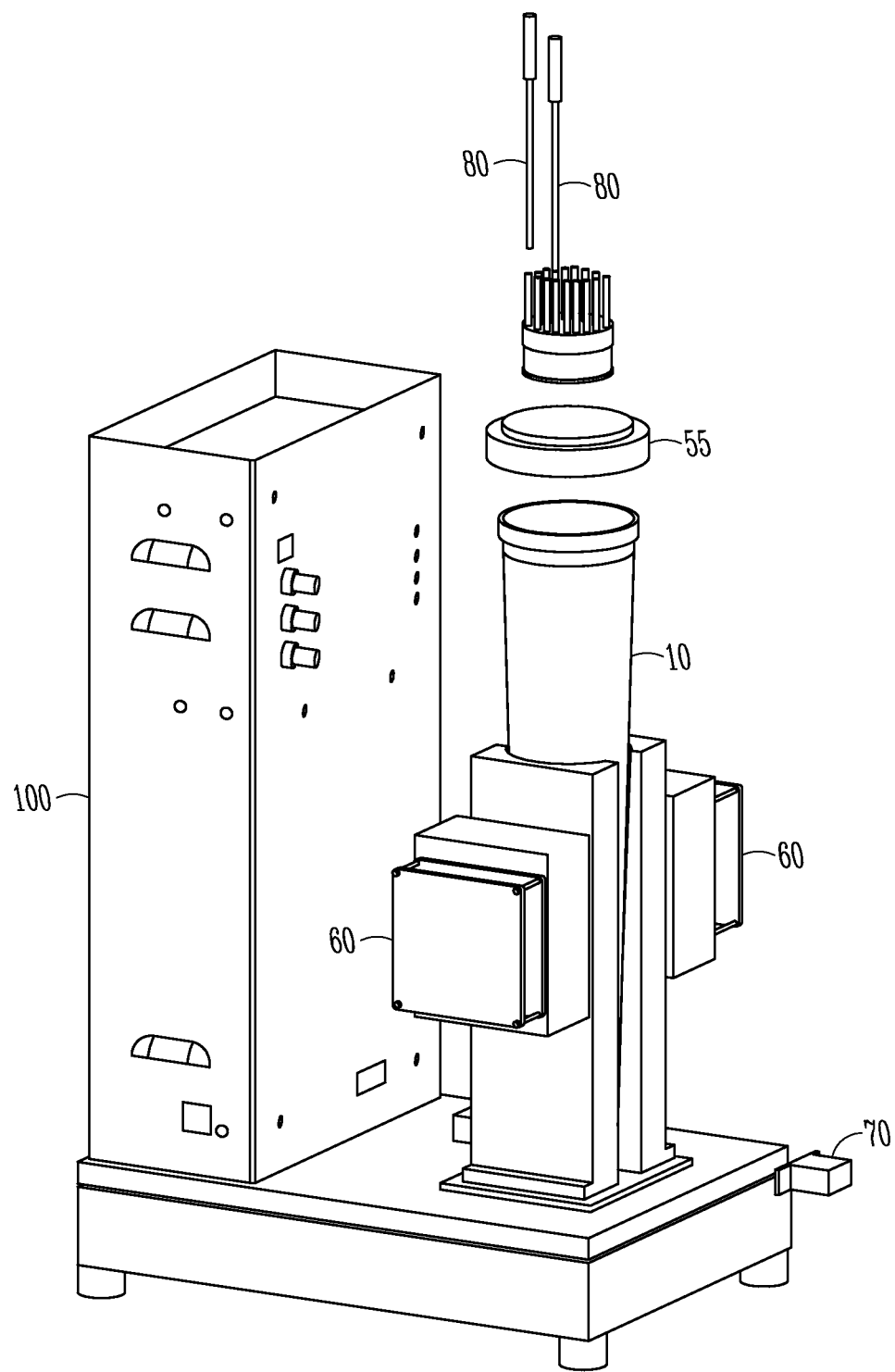
FIG. 4 is a dissembled view of some of the main parts of an ePBR system in an embodiment of the present invention.
Figure 5:
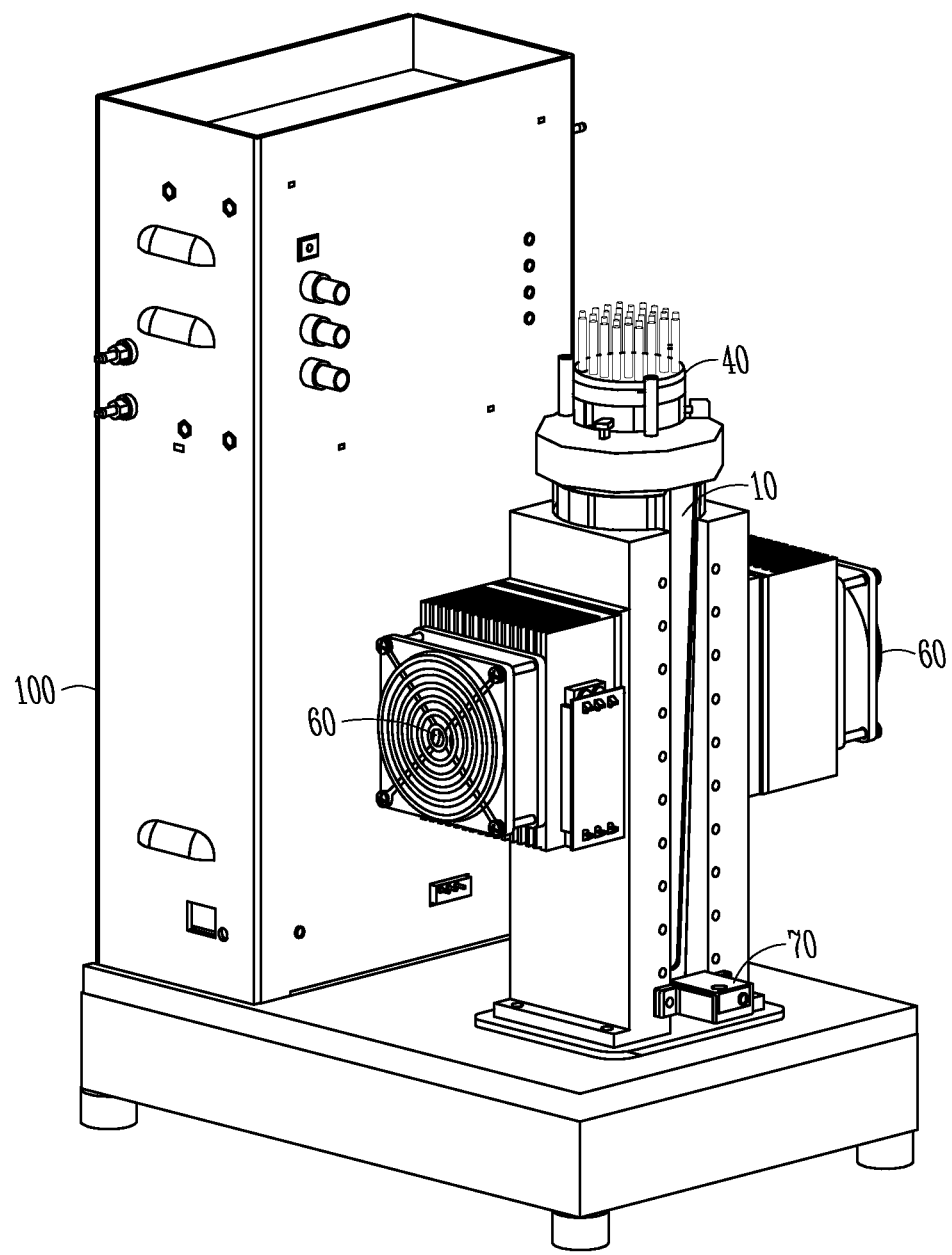
FIG. 5 is an assembled view of the PBR system of FIG. 4 in an embodiment of the present invention.
Figure 6:
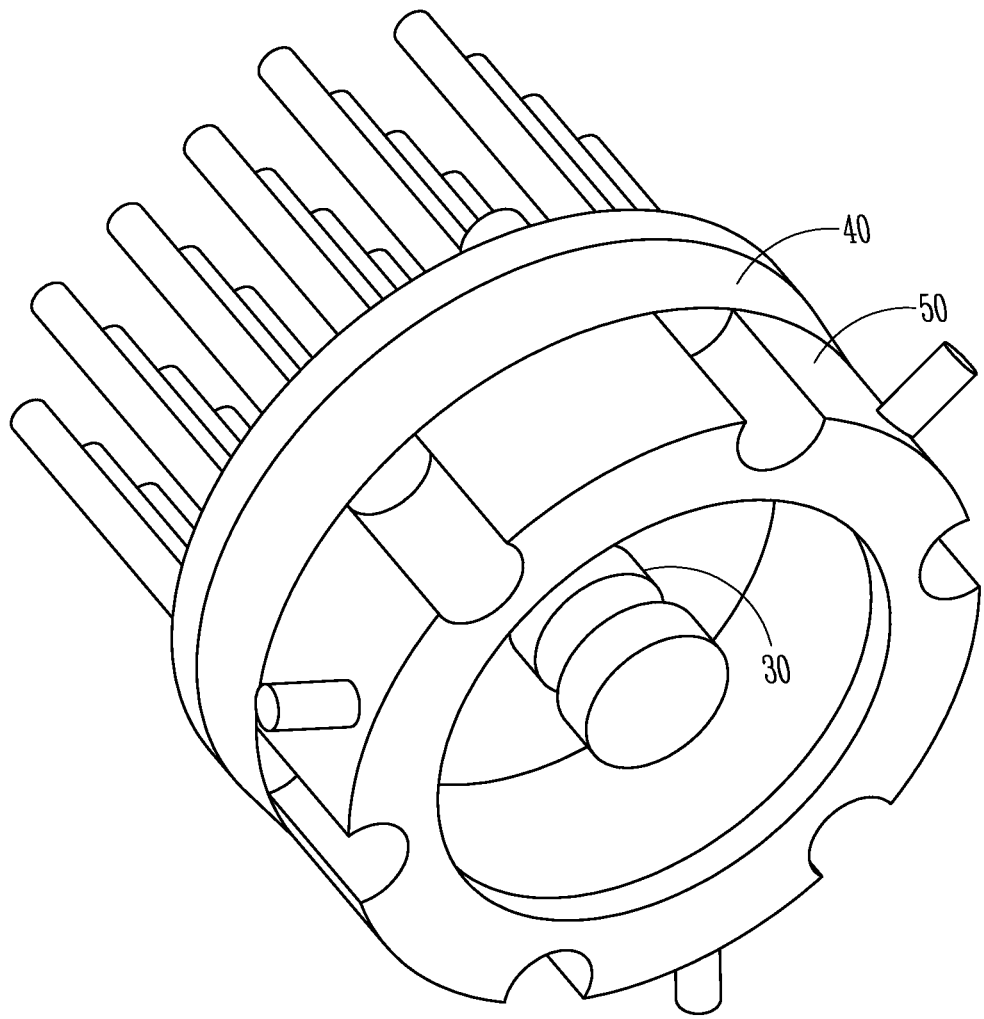
FIG. 6 is an assembled view of an ePBR lighting assembly in an embodiment of the present invention.
Figure 7:
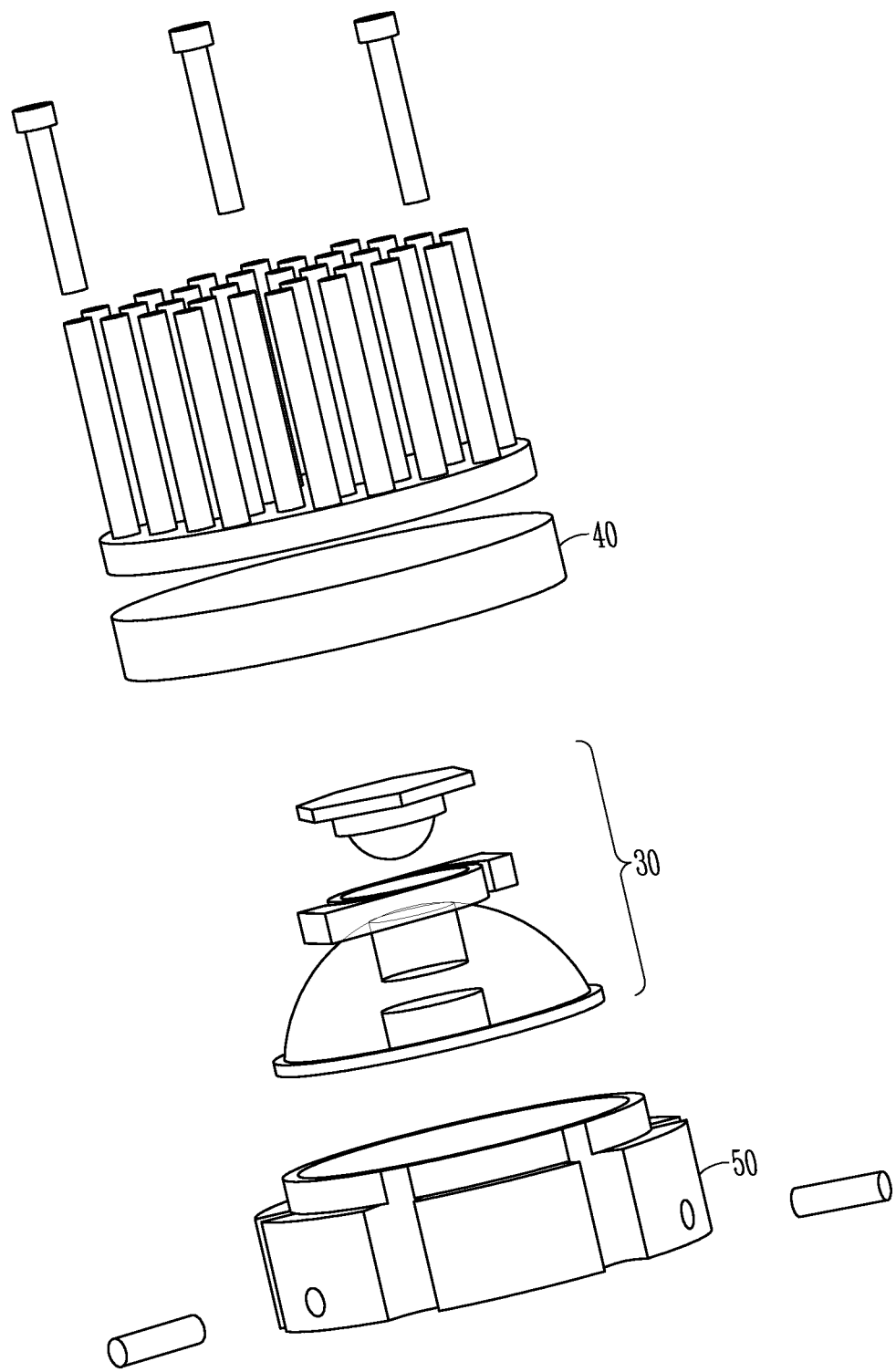
FIG. 7 is a dissembled view of some of the main parts of the lighting assembly of FIG. 6 in an embodiment of the present invention.

Additional testing is in progress using the model presented in FIGS. 2 and 3. The goal is to identify mechanisms in algae that are not required for growth under ideal conditions but that may facilitate survival of algae when subjected to short pulses of high-intensity light.

For this experiment, a 2×2 array of four photobioreactors is set up with constant temperature and aeration. One variable (or dimension) tested is strain, where the strains tested are either wild-type *Chlamydomonas* or various mutant strains. A second variable (or dimension) is light treatment, where either a normal day-night cycle is tested versus a day-night cycle with periodic bright flashes. In some examples, the bright flashes may have an intensity of 4000 micromole photons per $m^2$ per s for 10 second.

With each run, a different mutant is tested. Each of the mutants screened can have genetic mutations that may give to a deficiency in a photoprotective or adaptive response. For example, the mutant strains may respond differently to defined state transitions or to non-photochemical quenching. The growth of the mutant is compared with wild-type to determine if the mutated gene is important to short term light adaptation in algae.

Mutants with reduced non-photochemical quenching responses may have impaired growth (possibly severely impaired growth) when exposed to the bright flashes, but the mutants with state transition mutations will be unaffected. Mutants having constantly active photoprotective mechanisms may have slower growth over all, but may be less affected by the light pulses.

EXAMPLE 5 (PROPHETIC)

Photobioreactor Array Experiment

The increasing demand for renewable sources of liquid fuel has generated significant interest in the cultivation of microalgae. One of the key challenges to large-scale growth of algae is choosing the right species and the right strain to optimize productivity for the local climates existing at selected geographic locations (Ling Xu, Engineering in Life Sciences 9(3): 178-189 (2009)). Previous work by Ernesto Garcia-Mendoza et al. indicates that different mechanisms are used by algae to acclimate to light fluctuations as well as its intensity (Ernesto Garcia-Mendoza, Photosynthesis Res. 74: 303-315 (2002)).

This Example provides experimental procedures for addressing the affects of light fluctuations (e.g. the shadow of a passing cloud) on productivity in various types of algae. In particular, this Example is designed to examine the types of photoprotective strategies used by various algal species to fluctuations in darkness, using the environmental photobioreactor array (ePBRA) system shown in FIG. 1 with the photobioreactors described herein.

Experimental Procedures:

To assess which photoprotective mechanisms are used by photoautotrophic algae for adaptation to rapid changes in sunlight (such as a passing cloud) and gradual changes in sunlight (such as setting of the sun) multiple species/strains of algae will be tested. Algae of different species and/or strains that possess features useful for biofuel production will be grown at constant and varying frequencies of modulated light. Freshwater algal species such as *Chlorella* and *Botryococcus*, or strains thereof, will be tested initially. Optical density measurements will be performed continuously over time to determine growth. Periodic fluorescence measurements will be taken on probes dedicated to various photoprotective mechanisms in the algae.

A two-dimensional array of photobioreactors will be used to grow rows of algal strains (in one dimension) where the light conditions vary along the second dimension. In some experiments, the total illumination time (12 hours per 24 hour cycle) and/or the light intensity may be kept constant. For example, in some experiments the light conditions will vary in light/dark periodicity. The reactors will be kept at a substantially constant temperature and all strains will be grown in the same media (e.g., minimal salt media). Optical density (growth) and fluorescence measurements (photoprotection) will be recorded periodically by automated computer control. The algal cultures will be monitored until a stationary phase is reached.

Results:

Plotting algal growth rate at mid log phase (maximum growth rate) as a function light/dark periodicity should yield a sigmoidal curve, with one or more regions where growth is not substantially affected by changes in the period. The plateaus are expected to correspond to the kinetic rates of the different photoprotective mechanisms, such as non-photochemical quenching (NPQ), state transitions, pigment synthesis and gene regulation. When the periodicity is faster than a given mechanism, that mechanism will likely be either constantly active or constantly inactive.

EXAMPLE 6 (PROPHETIC)

Site-Targeted Strain Optimization

Additional testing for biofuel farming applications will be completed using an expanded environmental photobioreactor array (ePBRA) system shown in FIG. 1 with the photobioreactors described herein. The ePBRA will be used to select strains and sparging routines for a biofuels algal farm based in a particular geographical location.

Objectives:
 1) Selection of algal strain(s) with reliable growth and high productivity in a geographical microclimate for each season.
 2) Determination of optimal $CO_2$ sparging routine(s) to maximize productivity of selected strain(s).

Experimental Procedures:

A multi-dimensional array of ePBRs will be set up having rows of various algal strains (first dimension), different $CO_2$ sparging frequencies (second dimension) and seasonal growing conditions (third dimension). The seasonal growing conditions will vary in temperature, day length and light intensity, and these conditions will be modulated based on historical daily conditions of a given geographical location.

Various algal strains will be tested for hardiness and productivity, including local algal isolates from selected geographical regions. Examples of algal strains that will be tested include *Dunaliella* sp., *Chlorella* sp., *Spirulina* sp. and *Chloromonas* ANT3. Both control and mutant strains may be tested. All strains will be grown photosynthetically with continuous aeration in a minimal growth medium.

In the second dimension, cultures will be sparged with $CO_2$ for five (5) minute periods, varying the amount of $CO_2$ and the number of sparging events occurring throughout the daylight cycle.

Light intensities, duration of day and temperature will be set according to recorded values, obtained from the National Oceanic and Atmospheric Administration (NOAA) archives or other local climate archive.

For the another dimension, four sets of strain vs. sparging arrays will be set up for evaluating growth and productivity for any distinctive seasonal periods. Cultures will initially likely be grown to the beginning of stationary phase, at which point cell density will be maintained by periodic draining and replenishment of media.

Growth will be monitored using turbidity at 910 nm ($OD_{910}$) and/or by performing automated cell counts from samples collected from each reactor periodically. To evaluate productivity, oil content will be measured by mixing 1 ml aliquots of sample with the lipophilic dye Nile Red and measuring fluorescence.

Results:

If the selected location is in the northern hemisphere and has four distinctive seasons, such as a colder Fall and Winter, and a warmer Spring and Summer, amongst the four specified algae strains, *Chlorella* will have one of the highest productivities at high sparging frequencies. In such a scenario, the Antarctic isolate *Chloromonas* will likely have the highest growth rate and productivity in a cold winter season, but may quickly die out during the other seasons. At lower sparging frequencies, *Spirulina* will likely be more productive than *Chlorella*.

The various alga strains are expected to have better growth with increased sparging, but may become saturated at difference frequencies of sparging. See, Jaime Fábregas et al. Bioresource Technology 48: 107-111 (1994). However, each alga strain may have a point of diminishing return, where additional sparging does not lead to proportionately more productivity. The location of this threshold is likely to be different for each strain.

In order to meet the needs of future bioenergy and bioproducts, the systems and methods described herein allow testing of various parameters for various types of biomass and algal strains so that with new phenotypes can be generated. The novel embodiments describe herein provide an efficient, cost-effective and flexible system for testing a wide variety of parameters under real-life conditions of varying types of biomass.

In one embodiment, the novel system comprises a modular photobioreactor/sensor array containing two or more photobioreactors. In one embodiment, each of the photobioreactors is capable of measuring a number of physiological parameters (e.g., optical density of a biomass culture) continuously while maintaining high throughput (parallel) experimentation. In one embodiment, lighting is provided by collimated light emitting diodes (LEDs) to simulate the quality and penetration of natural sunlight, and can optionally include an automated computer control over the light intensity to any intensity from dark to the equivalent of full daylight. In one embodiment, aeration is provided to the culture by bubbling gas into the bottom of the container. In one embodiment, multiple reactors can be run from a single computer.

Although specific embodiments have been illustrated and described herein, it will be appreciated by those of ordinary skill in the art that any arrangement that is calculated to achieve the same purpose may be substituted for the specific embodiment shown. For example, although the biomass has been characterized primarily as a type of algae, the novel systems and methods described herein can be used for screening and characterizing other types of biomass, as noted herein. This application is intended to cover any adaptations or variations of the present subject matter. Therefore, it is manifestly intended that embodiments of this invention be limited only by the claims and the equivalents thereof.

References

Ling Xu, Pamela J. Weathers, Xue-Rong Xiong, Chun-Zhao Liu. *Microbial bioreactors: Challenges and opportunities.* Engineering in Life Sciences (2009) 9, No. 3, 178-189.

Ernesto Garcia-Mendoza, Hans C. P. Matthijs, Hendrik Schubert, Luuc R. Mur. *Non-photochemical quenching of chlorophyll fluorescence in Chlorella fusca acclimated to constant and dynamic light conditions.* Photosynthesis Research (2002) 74, 303-315.

Zhirong Li, Tae Kyu Ahn, Thomas J. Avenson, Matteo Ballottari, Jeffrey A. Cruz, David M. Kramer, Roberto Bassi, Graham R. Fleming, Jay D. Keasling, Krishna K. Niyogi. *Lutein Accumulation in the Absence of Zeaxanthin Restores Nonphotochemical Quenching in the Arabidopsis thaliana npq1Mutant.* The Plant Cell (2009) 21, 1798-1812.

Francis-André Wollman. *State transitions reveal the dynamics and flexibility of the photosynthetic apparatus.* The EMBO Journal (2001) 20, 3623-363.

Jaime Fábregas, Lucía Ferrón, Yolanda Gamallo, Estella Vecino, Ana Otero, Concepción Herrero. *Improvement of growth rate and cell productivity by aeration rate in cultures of the marine microalga Dunaliella tertiolecta.* Bioresource Technology (1994) 48: 107-111.

Phillip Greenspan, Eugene P. Mayer, Stanly D. Fowler. *Nile red: a selective fluorescent stain for intracellular lipid droplets.* The Journal of Cell Biology (1985) 100, 965-973.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods, devices and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a bioreactor" or "a nucleic acid" or "a polypeptide" includes a plurality of such bioreactors, nucleic acids or polypeptides (for example, a solution of nucleic acids or polypeptides or a series of nucleic acid or polypeptide preparations), and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The following statements of the invention are intended to characterize possible elements of the invention according to the foregoing description given in the specification. Because this application is a provisional application, these statements may become changed upon preparation and filing of a nonprovisional application. Such changes are not intended to affect the scope of equivalents according to the claims issuing from the nonprovisional application, if such changes occur. According to 35 U.S.C. §111(b), claims are not required for a provisional application. Consequently, the statements of the invention cannot be interpreted to be claims pursuant to 35 U.S.C. §112.

Statements Describing Embodiments of the Invention:

1. A system comprising one or more environmental photobioreactor arrays, each array containing two or more modular photobioreactors, wherein the system is adapted:
   a) to monitor and modulate conditions within two or more modular of the photobioreactors; and/or
   b) to measure one or more physiological parameters of a biomass contained within two or more modular of the photobioreactors.
2. The system of statement 1, wherein the biomass comprises a photosynthetic organism or a photosynthetic cell.
3. The system of statement 1 or 2, wherein the biomass comprises a *Protista* or prokaryotic species.
4. The system of any of statements 1-3, wherein the biomass comprises algae, complex algae, aquatic macroalgae, seaweed, plant cells, aquatic plants or a combination thereof.
5. The system of any of statements 1-4, wherein the biomass comprises algae.
6. The system of any of statements 1-5, wherein the conditions comprise temperature, pH, gas concentration, cell density, nutrient concentration, waste concentration, product concentration or a combination thereof.
7. The system of any of statements 1-6, wherein the physiological parameters of the biomass comprise photosynthetic productivity, biofuel production, biomass density, biomass growth rate, production of a selected product, waste production, absorption of one or more nutrient(s), absorption, processing of a test agent or a combination thereof.
8. The system of any of statements 1-7, wherein at least one of the modular photobioreactors comprises a first modular unit comprising an inner vessel for holding the biomass.
9. The system of any of statements 1-8, wherein at least one of the modular photobioreactors comprises a second modular unit comprising a sleeve that comprises a temperature control unit and one or more sensors.
10. The system of any of statements 1-9, wherein at least of the modular photobioreactors comprise components is selected from the group consisting of a vessel for biomass, a biomass agitator, a light source, a temperature control unit, one or more sensors, a liquid entry portal, a gas entry portal, a sampling station and a combination thereof.
11. The system of any of statements 1-10, wherein the system comprises a processor that transmits instructions to one or more components of the modular photobioreactors.
12. The system of any of statements 1-11, wherein the system comprises a processor that transmits instructions to one or more components of the modular photobioreactors after processing information received from one or more sensors in the modular photobioreactors.
13. The system of any of statements 1-12, wherein the system comprises one or more of the sensors comprising or consisting essentially of a detector adapted to detect temperature, pH, gas concentration, cell density, nutrient concentration, waste concentration, product concentration or a combination thereof.
14. The system of any of statements 1-13, wherein the system comprises a biomass agitator that comprises or consists essentially of a magnetic stirrer, sparger or a combination thereof.
15. The system of any of statements 1-14, wherein the system comprises a vessel adapted to be removable from a photobioreactor, filled with media, autoclaved and replaced within a photobioreactor.
16. The system of any of statements 1-15, wherein at least one photobioreactor comprises a vessel with media adapted for growth, maintenance and/or testing of the biomass.
17. The system of any of statements 1-16, wherein at least one photobioreactor comprises a vessel with a light source adapted to illuminate a column of water within the vessel.
18. The system of statement 17, wherein the column is adapted to mimic sunlight penetration in a natural body of water.
19. The system of any of statements 1-18, wherein the system is adapted for testing environmental conditions to optimize growth or photosynthetic activity of a selected biomass.
20. The system of any of statements 1-19, wherein the system is adapted for testing a series of biomass species or biomass strains under selected environmental conditions.
21. The system of any of statements 1-20, wherein the system is adapted to modulate and/or test conditions comprising temperature, pH, gas concentration, cell density, nutrient concentration, waste concentration, product concentration or a combination thereof.
22. The system of any of statements 1-21, wherein the system is adapted for testing absorption and/or processing of a drug, toxin, nutrient or waste material by the biomass.
23. The system of any of statements 1-22, wherein the system is adapted for testing absorption and/or processing of a gaseous manufacturing byproduct by the biomass.
24. The system of any of statements 1-23, wherein the system is adapted for testing absorption and/or processing of a gaseous manufacturing byproduct selected from the group consisting carbon dioxide, sulfur dioxide, nitrogen oxide or a combination thereof.
25. A method comprising testing and/or characterizing a biomass using the system of any of 1-24 to test and/or characterize the biomass.
26. The method of statement 25, wherein the conditions comprise temperature, pH, gas concentration, cell density, nutrient concentration, waste concentration, product concentration or a combination thereof.
27. The method of statement 25 or 26, wherein the physiological parameter of the biomass comprises photosynthetic productivity, biofuel production, biomass density, biomass growth rate, production of a selected product, waste production, absorption of one or more nutrient(s), absorption, processing of a test agent or a combination thereof.

28. The method of any of statements 25-27, wherein the physiological parameter of the biomass comprises a test agent selected from the group consisting of a toxin, carbon dioxide, a pharmaceutical or a combination thereof.

29. The method of any of statements 25-28, further comprising selecting environmental conditions for optimized growth or photosynthetic activity of a selected biomass.

30. The method of any of statement 25-29, further comprising selecting a biomass species or biomass strain for growth under a selected environmental condition.

31. A method comprising assessing production of a product from a biomass in a system comprising one or more environmental photobioreactor arrays, each array containing two or more modular photobioreactors, wherein the system is adapted:
   a) to monitor and modulate conditions within two or more modular photobioreactors to optimize production of the product; and
   b) to measure production of the product under conditions within two or more modular photobioreactors to thereby assess production of the product from a biomass.

32. The method of statement 31, further comprising extracting the product from a biomass.

33. The method of statement 31 or 32, wherein the product is an edible material, pharmaceutical, nutriceutical, protein, amino acid, fat, vitamin, oil, fiber, mineral, sugar, carbohydrate, alcohol or a combination thereof from the biomass.

34. The system of any of statements 31-33, wherein the biomass comprises a photosynthetic organism or a photosynthetic cell.

35. The system of any of statement 31-34, wherein the biomass comprises a *Protista* or prokaryotic species.

36. The system of any of statements 31-35, wherein the biomass comprises algae, complex algae, aquatic macroalgae, seaweed, plant cells, aquatic plants or a combination thereof.

37. The system of any of statements 31-36, wherein the biomass comprises algae.

38. The system of any of statements 31-37, wherein the conditions comprise temperature, pH, gas concentration, cell density, nutrient concentration, waste concentration, product concentration or a combination thereof.

39. The system of any of statements 31-38, wherein the physiological parameters of the biomass comprise photosynthetic productivity, biofuel production, biomass density, biomass growth rate, production of a selected product, waste production, absorption of one or more nutrient(s), absorption, processing of a test agent or a combination thereof.

40. The system of any of statements 31-39, wherein at least one of the modular photobioreactors comprises a first modular unit comprising an inner vessel for holding the biomass.

41. The system of any of statements 31-40, wherein at least one of the modular photobioreactors comprises a second modular unit comprising a sleeve that comprises a temperature control unit and one or more sensors.

42. The system of any of statements 31-41, wherein at least of the modular photobioreactors comprise components is selected from the group consisting of a vessel for biomass, a biomass agitator, a light source, a temperature control unit, one or more sensors, a liquid entry portal, a gas entry portal, a sampling station and a combination thereof.

43. The system of any of statements 31-42, wherein the system comprises a processor that transmits instructions to one or more components of the modular photobioreactors.

44. The system of any of statements 31-43, wherein the system comprises a processor that transmits instructions to one or more components of the modular photobioreactors after processing information received from one or more sensors in the modular photobioreactors.

45. The system of any of statements 31-44, wherein the system comprises one or more of the sensors comprising or consisting essentially of a detector adapted to detect temperature, pH, gas concentration, cell density, nutrient concentration, waste concentration, product concentration or a combination thereof.

46. The system of any of statements 31-45, wherein the system comprises a biomass agitator that comprises or consists essentially of a magnetic stirrer, sparger or a combination thereof.

47. The system of any of statements 31-46, wherein the system comprises a vessel adapted to be removable from a photobioreactor, filled with media, autoclaved and replaced within a photobioreactor.

48. The system of any of statements 31-47, wherein at least one photobioreactor comprises a vessel with media adapted for growth, maintenance and/or testing of the biomass.

49. The system of any of statements 31-48, wherein at least one photobioreactor comprises a vessel with a light source adapted to illuminate a column of water within the vessel.

50. The system of statement 49, wherein the column is adapted to mimic sunlight penetration in a natural body of water.

51. The system of any of statements 31-50, wherein the system is adapted for testing environmental conditions to optimize growth or photosynthetic activity of a selected biomass.

52. The system of any of statements 31-51, wherein the system is adapted for testing a series of biomass species or biomass strains under selected environmental conditions.

53. The system of any of statements 31-52, wherein the system is adapted to modulate and/or test conditions comprising temperature, pH, gas concentration, cell density, nutrient concentration, waste concentration, product concentration or a combination thereof.

54. The system of any of statements 31-53, wherein the system is adapted for testing absorption and/or processing of a drug, toxin, nutrient or waste material by the biomass.

55. The system of any of statements 31-54, wherein the system is adapted for testing absorption and/or processing of a gaseous manufacturing byproduct by the biomass.

56. The system of any of statements 31-55, wherein the system is adapted for testing absorption and/or processing of a gaseous manufacturing byproduct selected from the group consisting carbon dioxide, sulfur dioxide, nitrogen oxide or a combination thereof.

57. A biofuel comprising a biomass selected using the system of any of claims 1-24.

58. A method of extracting a biofuel from a biomass comprising:
   a) obtaining an aqueous suspension of biomass from the system of any of statements 1-24;

b) adding to the aqueous suspension of biomass at least one organic solvent immiscible or substantially immiscible with water to generate an organic-aqueous mixture;

c) subjecting the organic-aqueous mixture to evaporation of water and biofuel extraction, to thereby obtain:
  (i) an organic phase comprising biofuels and the organic solvent;
  (ii) a semi-solid phase comprising a residue of the biomass.

59. The method of statement 58, wherein evaporation operates at a temperature that yields substantially complete removal of the water from the organic-aqueous mixture.

60. The method of statement 58 or 59, wherein the biofuel is a lipid or a mixture of lipids.

61. The method of any of statements 58-60, wherein the solvent is an aliphatic hydrocarbon.

62. The method of any of statements 58-60, wherein the solvent is an aliphatic hydrocarbon selected from the group of aliphatic hydrocarbons having a boiling point higher than 100° C.

63. The method of any of statements 58-60, wherein the solvent is hexane, chloroform, n-octane, nonane, decane, or mixtures thereof.

64. The method of any of statements 58-60, wherein the solvent is an aromatic hydrocarbon.

65. The method of any of statements 58-60, wherein the solvent is a xylene isomer, toluene, benzene, chlorobenzene, or mixtures thereof.

66. The method of any of statements 58-60, wherein the solvent is a refinery cut.

67. The method of any of statements 58-60, wherein the solvent is a mixture of the aliphatic hydrocarbons.

68. The method of any of statements 58-60, wherein the solvent is a mixture of the aliphatic hydrocarbons, where the mixture has a boiling point higher than 100° C.

69. The method of any of statements 58-60, wherein the solvent is a mixture of the aromatic hydrocarbons.

70. The method of any of statements 58-60, wherein the solvent is a mixture of aliphatic and aromatic hydrocarbons.

71. The method of any of statements 58-60, wherein the solvent is hexane, chloroform, n-octane, nonane, decane, or mixtures thereof; an aromatic hydrocarbon such as xylene isomers, toluene, benzene, chlorobenzene, or mixtures thereof; refinery cuts such as: (a) mixtures of the aliphatic hydrocarbons, where the mixtures have a boiling point higher than 100° C., (b) mixtures of the aromatic hydrocarbons, and (c) mixtures of such aliphatic and aromatic hydrocarbons.

Other embodiments are described within the following claims.

What is claimed is:

1. A photobioreactor system comprising:
an array of analytical laboratory-scale photobioreactors comprising a plurality of environmental vertically oriented photobioreactor vessels, each having a vessel top equipped with a lighting system comprising variable LED lighting, wherein each lighting system is configured to operate at a different intensity or intensity range within each vessel in order to simulate different natural lighting conditions within each vessel, including sunlight penetration in a natural body of water, and sunlight intensity; and
a processor operably connectable to said array with a connector and configured to separately monitor, modulate and record the light intensity, the light penetration, and other environmental conditions within each vessel and to measure and record multiple physiological parameters of different types of biomass containable within each vessel substantially simultaneously.

2. The system of claim 1, wherein at least one of the different types of biomass comprises a photosynthetic organism or a photosynthetic cell.

3. The system of claim 1, wherein at least one of the different types of biomass comprises a *Protista* or prokaryotic species.

4. The system of claim 1, wherein the different types of biomass comprise complex algae, aquatic macroalgae, seaweed, plant cells, aquatic plants or a combination thereof.

5. The system of claim 1, wherein at least one of the different types of biomass comprises algae.

6. The system of claim 1, wherein the other environmental conditions comprise temperature, aeration, pH, gas concentration, cell density, nutrient concentration, waste concentration, product concentration or a combination thereof.

7. The system of claim 1, wherein the physiological parameters of each of the different types of biomass comprise photosynthetic activity, biomass density, biomass growth rate, product production, waste production, absorption, secretion of waste and/or one or more products, processing of a test agent processing of a gaseous manufacturing byproduct, processing of one or more waste materials, or a combination thereof.

8. The system of claim 1, wherein the array further comprises components in communication with each vessel and with the processor, wherein the components are selected from lighting system components, temperature control units, biomass agitators, sensors, liquid entry portals, gas entry portals, sampling devices, electrodes, and a combination thereof.

9. The system of claim 8, wherein the temperature control unit comprises one or more jackets configured to surround one or more vessels, a temperature controlled water bath configured to receive one or more vessels, or a combination thereof.

10. The system of claim 8, wherein the processor is configured to transmit instructions to the components.

11. The system of claim 10, wherein the processor is configured to transmit the instructions to the components after processing information received from the sensors.

12. The system of claim 8, wherein the sensors are monitoring sensors comprising detectors configured to detect the physiological parameters of the different types of biomass and the environmental conditions.

13. The system of claim 8, wherein said biomass agitators comprise one or more magnetic stirrers, one or more spargers or a combination thereof.

14. The system of claim 1, wherein each vessel is a modular vessel configured to be removable from the array, filled with media, autoclaved and returned to the array.

15. The system of claim 1, wherein each vessel contains media adapted for growth, maintenance or testing of the biomass.

16. The system of claim 1, wherein the system is configured to test different environmental conditions and identify optimal environmental conditions for growth of a selected biomass, product production from a selected biomass, or a combination thereof.

17. The system of claim 1, wherein the system is configured to test a series of biomass species and/or biomass strains under different environmental conditions, to identify optimal environmental conditions for growth of different types of biomass species and/or strains, to identify optimal biomass species and/or strains for growth in a given set of environmental conditions, or a combination thereof.

18. The system of claim 7, wherein the absorption comprises nutrient absorption, toxin absorption, carbon dioxide absorption, pharmaceutical absorption or a combination thereof and/or the processing of a test agent comprises processing of growth modulators, metals, environmental chemicals, toxins, pharmaceuticals, carbon dioxide, nutrients or a combination thereof by the biomass.

19. The system of claim 7, wherein the gaseous manufacturing byproduct is carbon dioxide, sulfur dioxide, nitrogen oxide or a combination thereof.

20. A photobioreactor apparatus comprising:
an array of analytical laboratory-scale photobioreactors comprising a plurality of environmental vertically oriented photobioreactor vessels, each having a vessel top equipped with a lighting system comprising variable LED lighting, wherein each lighting system is configured to operate at a different intensity or intensity range within each vessel in order to simulate different natural lighting conditions within each vessel, including sunlight penetration in a natural body of water and sunlight intensity, each array containing two or more modular photobioreactors, wherein the apparatus is configured to monitor and modulate conditions within each modular photobioreactor, and to measure one or more physiological parameters of a biomass contained therein, identify optimal environmental conditions for growth of different types of biomass species and/or strains, identify optimal biomass species and/or strains for growth in a given set of environmental conditions, or a combination thereof, wherein at least one of said modular photobioreactors contains a biomass agitator.

21. The system of claim 1 wherein the connector also connects one or more sensors to the processor, the processor to the vessel, the processor to one or more temperature control units or any combination thereof.

22. The system of claim 21 wherein at least one of said sensors is a multi-component sensor that transmits or releases a stimulus and a second component that detects a response to the stimulus.

23. The system of claim 1 wherein at least some of the vessels have a side equipped with one or more ribs.

24. The system of claim 1 wherein at least some of the vessels have a conical shape.

25. The system of claim 1 wherein each vessel can hold from about 2 ml to about 300 ml.

26. The system of claim 1 wherein each vessel has a culture depth from about 5 to about 45 cm.

27. The system of claim 1 wherein the light intensity and light penetration is monitored and modulated within each vessel with light sensors.

28. The system of claim 1 wherein the array is arranged in parallel, in a two-dimensional configuration or in a three-dimensional configuration.

29. The system of claim 1 wherein the variable LED lighting is collimated variable LED lighting.

30. The system of claim 1 further comprising a phenotyping apparatus.

31. The system of claim 1 further comprising one or more microprocessors operably connectable to at least some of the vessels.

32. The system of claim 31 further comprising software in communication with the system and executable on a suitable computer or series of computers.

33. The system of claim 7 wherein the cell density is monitored via in vivo spectroscopy.

34. The system of claim 7 wherein the photosynthetic activity in each vessel is measured by monitoring parameters selected from chlorophyll fluorescence, absorbance changes, carbon dioxide gas exchange, dissolved oxygen, pH, temperature, cell density, rough pigment content, light penetration through each vessel and a combination thereof.

35. The system of claim 7 wherein the product is biofuel.

36. The system of claim 8 wherein said sampling devices are nutrient sampling devices, gas sampling devices or a combination thereof.

37. The system of claim 12 wherein said monitoring sensors comprise one or more temperature sensors, one or more aeration sensors, one or more electrodes, one or more photodetectors, one or more gas flow detectors, one or more gas concentration detectors, one or more optical sensors, or a combination thereof.

38. The system of claim 37 wherein said electrodes include pH electrodes.

* * * * *

UNITED STATES PATENT AND TRADEMARK OFFICE
CERTIFICATE OF CORRECTION

PATENT NO.        : 9,816,065 B2                                    Page 1 of 1
APPLICATION NO.   : 13/988893
DATED             : November 14, 2017
INVENTOR(S)       : David Kramer et al.

It is certified that error appears in the above-identified patent and that said Letters Patent is hereby corrected as shown below:

In the Specification

Column 1/Line 15: "under." should read as "under"
Column 4/Line 15: "ePBR allow" should read as "ePBR allows"
Column 10/Line 48: "(20) is to" should read as "(20) to"
Column 11/Line 22: "etc. by" should read as "etc., by"
Column 11/Line 24: "etc. by" should read as "etc., by"
Column 14/Line 56: "10 second" should read as "10 seconds"
Column 16/Line 43: "For the another" should read as "For the other"
Column 17/Line 59: "npq1Mutant." should read as "npq1 Mutant."
Column 17/Line 62: "3623-363" should read as "3623-3630"

Signed and Sealed this
Twenty-seventh Day of March, 2018

Andrei Iancu
*Director of the United States Patent and Trademark Office*